(12) United States Patent
Tsusaka et al.

(10) Patent No.: US 10,376,318 B2
(45) Date of Patent: Aug. 13, 2019

(54) SURGICAL ASSISTANCE APPARATUS, PROGRAM, STORAGE MEDIUM, AND SURGICAL ASSISTANCE METHOD

(71) Applicant: KYOCERA Medical Corporation, Osaka-shi, Osaka (JP)

(72) Inventors: Shinya Tsusaka, Osaka (JP); Masahiko Hashida, Osaka (JP)

(73) Assignee: KYOCERA CORPORATION, Kyoto (JP)

( * ) Notice: Subject to any disclaimer, the term of this patent is extended or adjusted under 35 U.S.C. 154(b) by 31 days.

(21) Appl. No.: 15/329,763

(22) PCT Filed: Sep. 14, 2015

(86) PCT No.: PCT/JP2015/076014
§ 371 (c)(1),
(2) Date: Jan. 27, 2017

(87) PCT Pub. No.: WO2016/052157
PCT Pub. Date: Apr. 17, 2016

(65) Prior Publication Data
US 2017/0215966 A1 Aug. 3, 2017

(30) Foreign Application Priority Data
Sep. 30, 2014 (JP) .................. 2014-202285

(51) Int. Cl.
*A61B 34/10* (2016.01)
*A61B 17/00* (2006.01)
(Continued)

(52) U.S. Cl.
CPC .............. *A61B 34/10* (2016.02); *A61B 17/56* (2013.01); *A61B 34/25* (2016.02); *A61B 90/00* (2016.02);
(Continued)

(58) Field of Classification Search
CPC ........... A61B 34/10; A61B 1/00; A61B 17/00; A61B 18/00
See application file for complete search history.

(56) References Cited

U.S. PATENT DOCUMENTS 5,772,593 A * 6/1998 Hakamata .............. A61B 90/36
348/77
6,690,964 B2 2/2004 Bieger et al.
(Continued)

FOREIGN PATENT DOCUMENTS

JP 09-024053 A 1/1997
JP 2002-102251 A 4/2002
(Continued)

OTHER PUBLICATIONS

International Search Report, PCT/JP2015/076014, dated Dec. 22, 2015, 2 pgs.
(Continued)

*Primary Examiner* — Yi Yang
(74) *Attorney, Agent, or Firm* — Volpe and Koenig, P.C.

(57) ABSTRACT

Provided is a surgical assistance apparatus and so on that make it possible to more accurately check the state that an affected part is to be in after a surgical operation has started, in advance of the surgical operation. A surgical assistance apparatus includes an image processing unit. The image processing unit creates projection image data based on measurement data that has been obtained by measuring an affected part of a patient, and thus creates a projection image as an image that is specified by the projection image data. This projection image is an image that is to be projected onto the patient, and includes an image that shows a state that the affected part is to be in after a surgical operation has started.

7 Claims, 32 Drawing Sheets

(51) Int. Cl.

| | | |
|---|---|---|
| *A61B 18/00* | (2006.01) | |
| *A61B 17/56* | (2006.01) | |
| *A61B 90/00* | (2016.01) | |
| *A61B 34/00* | (2016.01) | |
| *G06K 9/20* | (2006.01) | |
| *G06T 3/00* | (2006.01) | |
| *G06T 3/60* | (2006.01) | |
| *G06T 11/60* | (2006.01) | |
| *G06F 19/00* | (2018.01) | |

(52) U.S. Cl.
CPC ............ *A61B 90/06* (2016.02); *A61B 90/361* (2016.02); *G06F 19/30* (2013.01); *G06K 9/2054* (2013.01); *G06T 3/0068* (2013.01); *G06T 3/60* (2013.01); *G06T 11/60* (2013.01); *A61B 2017/564* (2013.01); *A61B 2034/105* (2016.02); *A61B 2034/107* (2016.02); *A61B 2090/366* (2016.02); *G06T 2210/41* (2013.01)

(56) References Cited

U.S. PATENT DOCUMENTS

| | | | |
|---|---|---|---|
| 8,126,533 | B2 | 2/2012 | Lavallee |
| 8,626,267 | B2 | 1/2014 | Lavallee |
| 8,880,152 | B2 | 11/2014 | Lavallee |
| 9,050,132 | B2 | 6/2015 | Lavallee |
| 9,220,571 | B2 | 12/2015 | Lavallee |
| 2002/0077533 | A1 | 6/2002 | Bieger et al. |
| 2005/0101966 | A1* | 5/2005 | Lavallee .............. A61B 17/154 606/102 |
| 2007/0185498 | A2 | 8/2007 | Lavallee |
| 2008/0319275 | A1* | 12/2008 | Chiu .................... A61B 5/0002 600/300 |
| 2012/0053443 | A1* | 3/2012 | Sakuragi ................ A61B 19/50 600/407 |
| 2012/0165706 | A1 | 6/2012 | Lavallee |
| 2014/0187912 | A1* | 7/2014 | Wang ................. G01R 33/4812 600/411 |
| 2014/0188121 | A1 | 7/2014 | Lavallee |
| 2015/0051478 | A1 | 2/2015 | Lavallee |
| 2015/0230877 | A1 | 8/2015 | Lavallee |
| 2016/0106554 | A1 | 4/2016 | Lavallee |

FOREIGN PATENT DOCUMENTS

| | | |
|---|---|---|
| JP | 2002-253574 A | 9/2002 |
| JP | 2004-512136 A | 4/2004 |
| JP | 2009-136426 A | 6/2009 |
| WO | 2013/096440 A1 | 6/2013 |

OTHER PUBLICATIONS

Projection Mapping Using Mixed Augmented Reality Surgery by OsiriX: Image Overlay Surgery, [online], [Feb. 1, 2012], internet<URL: https://www.youtube.com/watch?v=iTtg3vhgLVc>.

Fumihito Ito et al, "Image Registration to Generate an Upright 3D Knee Joint Model from a CT Image", The Journal of the Institute of Image Electronics Engineers of Japan, vol. 39, No. 5, pp. 706-713, Sep. 25, 2010 and its partial translation.

* cited by examiner

FRONT VIEW OF PATIENT

PROJECTION IMAGE IS PROJECTED
ONTO FRONT SURFACE OF PATIENT

FRONT VIEW OF PATIENT

SIDE VIEW OF PATIENT

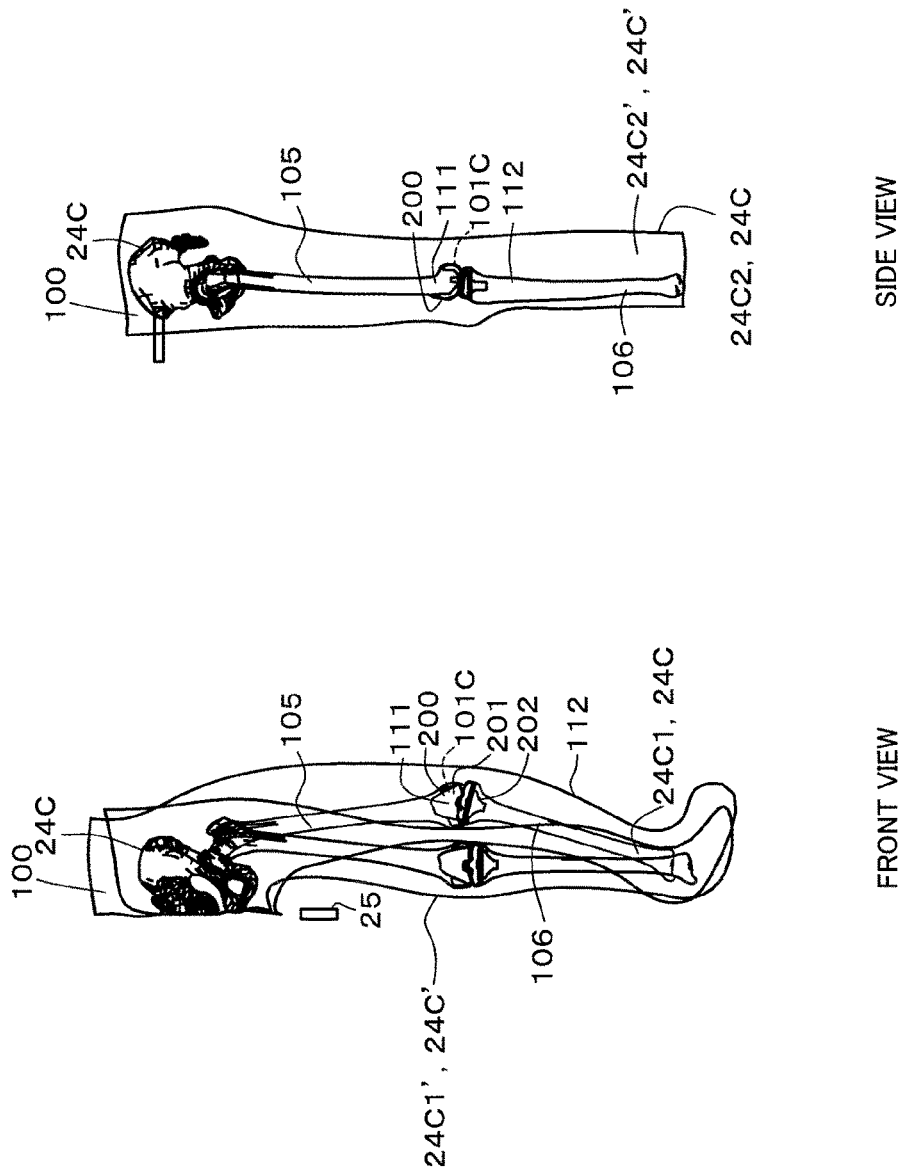

PROJECTION IMAGES ARE PROJECTED ONTO PATIENT

SURGICAL ASSISTANCE APPARATUS, PROGRAM, STORAGE MEDIUM, AND SURGICAL ASSISTANCE METHOD

TECHNICAL FIELD

The present invention relates to a surgical assistance apparatus, a program, a storage medium, and a surgical assistance method for assisting a surgeon in performing a surgical operation on a patient.

BACKGROUND ART

A mixed reality surgery is known as a surgical method that is used by a surgeon to perform a surgical operation on a patient (for example, see Non-Patent Document 1). According to this surgical method, a surgeon performs a surgical operation in a situation where images of blood vessels and organs are projected onto the body surface of a patient by a projector. By using images that are projected onto the body surface of a patient in such a manner, the surgeon can grasp the position of the organ that is to be subjected to a surgical operation, in advance of the surgical operation. Therefore, the surgeon can more accurately and more easily perform a surgical operation on the patient.

CITATION LIST

Patent Document

Non-Patent Document 1: Projection Mapping Using Mixed Augmented Reality Surgery by OsiriX: Image Overlay Surgery, [online], [Feb. 1, 2012], Internet <URL: https://www.youtube.com/watch?v=iTtg3vhgLVc>

DISCLOSURE OF THE INVENTION

Problem to be Solved by the Invention

In some kinds of surgical operations, such as: a knee joint operation, by which a deformed knee joint of a patient who suffers from knee osteoarthritis is restored towards an almost normal state; an artificial knee joint replacement, by which the knee joint of a patient is replaced with an artificial knee joint; and resection, by which an internal organ of a patient is excised, the shape of an affected part of the patient after a surgical operation differs from the shape before the surgical operation. Therefore, it is preferable that the surgeon more accurately checks the shape that the affected part will take on after a surgical operation has started, in advance of the surgical operation.

However, the above-described prior art merely discloses that a preoperative state of the patient is displayed on the surface of the patient, and does not disclose a configuration for displaying the state that the patient is to be in after the surgical operation has started, in the case where the shape of the affected part after the surgical operation differs from the shape before the surgical operation.

In light of the above-described situation, the present invention aims to provide a surgical assistance apparatus, a program, a storage medium, and a surgical assistance method that make it possible to more accurately check the state that an affected part is to be in after a surgical operation has started, in advance of the surgical operation.

Means for Solving the Problem (1) A surgical assistance apparatus according to an aspect of the present invention for achieving the above-described aim includes an image processing unit, wherein the image processing unit is configured to create predetermined projection image data based on measurement data that has been obtained by measuring an affected part of a patient, and thus create a projection image as an image that is specified by the projection image data, and the projection image is an image that is to be projected onto the patient, and includes an image that shows the state that the affected part is to be in after a surgical operation has started.

With this configuration, the projection image that is to be projected onto the patient includes an image (a guide image) that shows the affected part at the time after a surgical operation on the affected part has started. Therefore, due to this projection image being projected onto the patient, the surgeon can more accurately check the shape that the affected part will take on after the surgical operation has started, in advance of the surgical operation. As a result, the surgeon can more accurately perform a surgical operation on the patient. Thus, with the present invention, it is possible to realize a surgical assistance apparatus that allows a surgeon to more accurately check the state that an affected part is to be in after a surgical operation has started, in advance of the surgical operation.

(2) Preferably, the image processing unit includes a region setting unit and a processing unit, the region setting unit is configured to set a predetermined processing candidate region out of a measurement image that is specified by the measurement data, and the processing unit is configured to create a predetermined processed image by applying predetermined processing to the processing candidate region, and subsequently create the projection image by performing processing to combine the processed image with an image other than the processing candidate region out of the measurement image.

With this configuration, the projection image shows how the affected part of the patient and a portion around the affected part are to be coupled to each other. Therefore, the surgeon can more accurately check, in advance, the state that the patient is to be in after a surgical operation has started, by referring to the projection image projected onto the patient.

(3) More preferably, the image processing unit is configured to receive the measurement data that specifies the measurement image that includes an image of a femur and an image of a tibia of the patient, the region setting unit is configured to set, as the processing candidate region, at least one of: a first processing candidate region that includes the image of the femur; and a second processing candidate region that includes the image of the tibia, and the processing unit is configured to create the processed image by applying the processing that includes rotation processing, to the processing candidate region.

With this configuration, when performing a surgical operation on a patient suffering from knee osteoarthritis, it is possible to realize a projection image that shows the state that the patient is to be in after the surgical operation has started. Consequently, the surgeon can more accurately perform a surgical operation for knee osteoarthritis.

(4) Preferably, the image processing unit is configured to receive the measurement data that specifies the measurement image that includes an image of a femur and an image of a tibia of the patient, and the processing unit is configured to create the projection image in which a center point of a caput, a center point of a knee joint, and a center point of an ankle in the measurement image are shown so as to be aligned in a straight line.

With this configuration, when performing a surgical operation for knee osteoarthritis or when performing a total knee replacement, the surgeon can more accurately check a positional state that the affected part should take on, in advance of the surgical operation. In particular, the surgeon can visually check the positions of the center points of the capita that cannot be directly seen while the surgeon is performing the surgical operation.

(5) Preferably, the processing unit is configured to create the projection image such that the projection image includes an image of an indicator that is provided on a body part that serves as a referential body part of the patient when the measurement image is captured.

With this configuration, it is possible to adjust the position of each part of the projection image to the actual position at which the part will be located after the surgical operation on the patient has started, by overlaying the image of the indicator, included in the projection image, upon the referential body part (the actual indicator) of the patient. Consequently, the surgeon can more accurately check how the affected part is to be treated after the surgical operation has started.

(6) Preferably, the image processing unit is configured to create, as the projection image, at least one of an intraoperative image and a postoperative image of the affected part.

With this configuration, if the projection image includes an intraoperative image of the affected part, the surgeon can more accurately check the intraoperative state of the affected part. Also, if the projection image includes a postoperative image of the affected part, the surgeon can more accurately check the postoperative state of the affected part.

(7) More preferably, the image processing unit is configured to create, as the projection image, an image for which the measurement data of the affected part is yet to be processed.

With this configuration, due to the projection image being projected onto the patient, the surgeon can check both the preoperative state and the state after the surgical operation has started. Consequently, the surgeon can more accurately and easily perform a surgical operation.

(8) Preferably, the image processing unit is configured to create, as the projection image, an image that includes at least one of: an image of an implant that is to be placed in the affected part; and an osteotomy line.

With this configuration, when performing implant placement, the surgeon can more accurately check the state that the affected part is to be in after a surgical operation has started, in advance of the surgical operation.

(9) Preferably, the surgical assistance apparatus further includes an operation apparatus for outputting operation data that operates the measurement data, to the image processing unit; and an image display apparatus for projecting the projection image onto the patient.

With this configuration, the surgical assistance apparatus can create a projection image that is desired by the surgeon upon, for example, the surgeon operating the operation apparatus. Also, this projection image can be projected onto the patient by using the image display apparatus.

(10) A program according to an aspect of the present invention for achieving the above-described aim is a program that causes a computer to execute an image processing step. The image processing step is a step in which predetermined projection image data is created based on measurement data that has been obtained by measuring an affected part of a patient, and thus a projection image is created as an image that is specified by the projection image data, and the projection image is an image that is to be projected onto the patient, and includes an image that shows a state that the affected part is to be in after a surgical operation has started.

With this configuration, the projection image that is to be projected onto the patient includes an image (a guide image) that shows the affected part at the time after a surgical operation on the affected part has started. Therefore, due to this projection image being projected onto the patient, the surgeon can more accurately check the shape that the affected part will take on after the surgical operation has started, in advance of the surgical operation. As a result, the surgeon can more accurately perform a surgical operation on the patient. Thus, with the present invention, it is possible to realize a program that allows a surgeon to more accurately check the state that an affected part is to be in after a surgical operation has started, in advance of the surgical operation.

(11) A storage medium according to an aspect of the present invention for achieving the above-described aim is a storage medium in which a program is stored and that is readable by a computer. The program is a program that causes the computer to execute an image processing step. The image processing step is a step in which predetermined projection image data is created based on measurement data that has been obtained by measuring an affected part of a patient, and thus a projection image is created as an image that is specified by the projection image data, and the projection image is an image that is to be projected onto the patient, and includes an image that shows a state that the affected part is to be in after a surgical operation has started.

With this configuration, the projection image that is to be projected onto the patient includes an image (a guide image) that shows the affected part at the time after a surgical operation on the affected part has started. Therefore, due to this projection image being projected onto the patient, the surgeon can more accurately check the shape that the affected part will take on after the surgical operation has started, in advance of the surgical operation. As a result, the surgeon can more accurately perform a surgical operation on the patient. Thus, with the present invention, it is possible to realize a storage medium that stores a program that allows a surgeon to more accurately check the state that an affected part is to be in after a surgical operation has started, in advance of the surgical operation.

(12) A surgical assistance method according to an aspect of the present invention for achieving the above-described aim includes an image processing step in which predetermined projection image data is created based on measurement data that has been obtained by measuring an affected part of a patient, and thus a projection image is created as an image that is specified by the projection image data, wherein the projection image is an image that is to be projected onto the patient, and includes an image that shows a state that the affected part is to be in after a surgical operation has started.

With this configuration, the projection image that is to be projected onto the patient includes an image (a guide image) that shows the affected part at the time after a surgical operation on the affected part has started. Therefore, due to this projection image being projected onto the patient, the surgeon can more accurately check the shape that the affected part will take on after the surgical operation has started, in advance of the surgical operation. As a result, the surgeon can more accurately perform a surgical operation on the patient. Thus, with the present invention, it is possible to realize a surgical assistance method that allows a surgeon to more accurately check the state that an affected part is to be in after a surgical operation has started, in advance of the surgical operation.

Effects of the Invention

With the present invention, a surgeon can more accurately check the state that an affected part is to be in after a surgical operation has started, in advance of the surgical operation.

BRIEF DESCRIPTION OF THE DRAWINGS

FIG. 11 shows a front view and a side view illustrating image processing that is performed by using the surgical assistance apparatus, and shows a situation in which two projection images are projected onto the patient.

DESCRIPTION OF EMBODIMENTS

The following describes an embodiment for carrying out the present invention with reference to the drawings. The present invention is broadly applicable, as a surgical assistance apparatus, a program, a storage medium, and a surgical assistance method.

Figure 1:
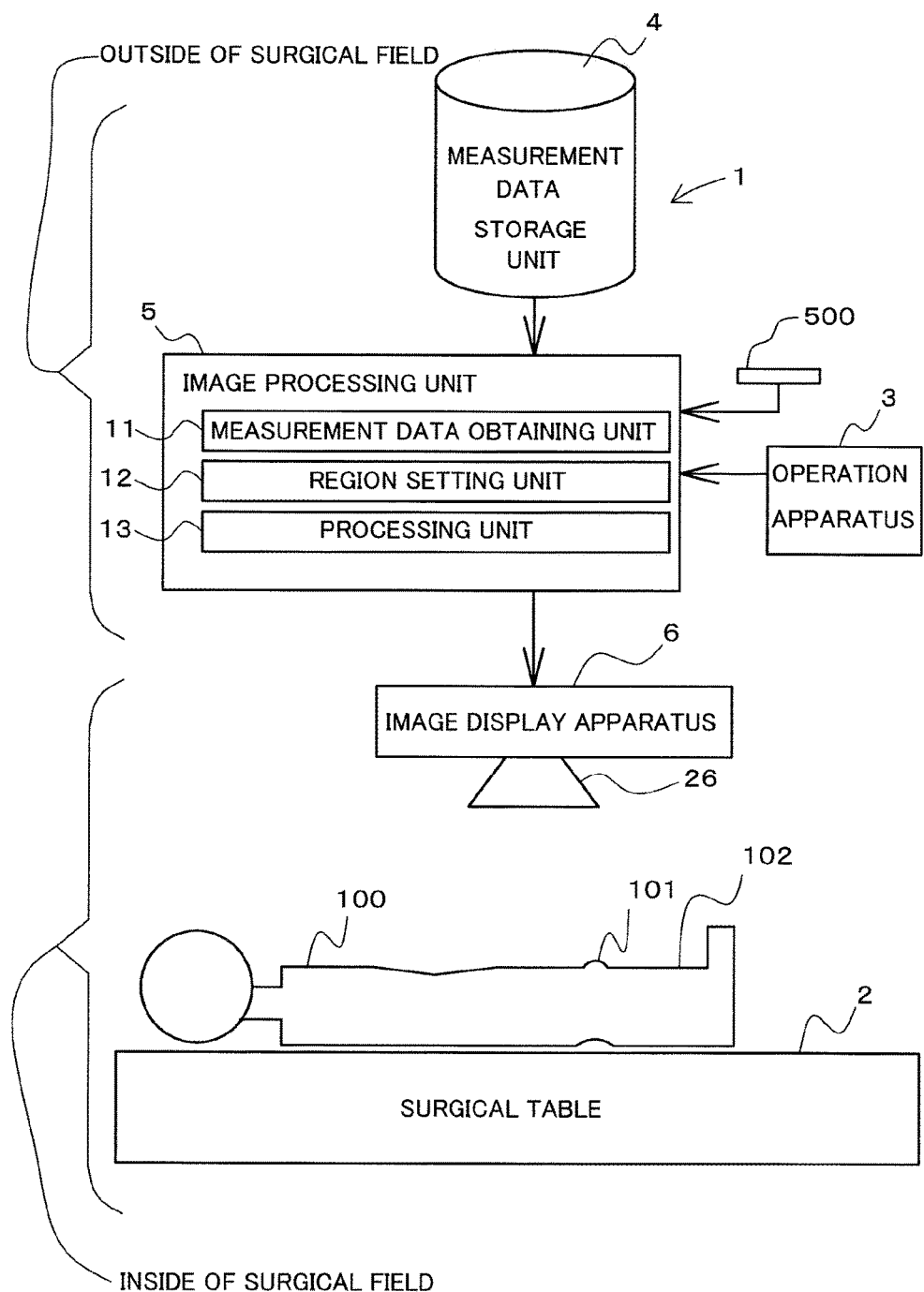
FIG. 1 is a schematic diagram showing a surgical assistance apparatus according to an embodiment of the present invention, a surgical table, and a patient.
Figure 2:
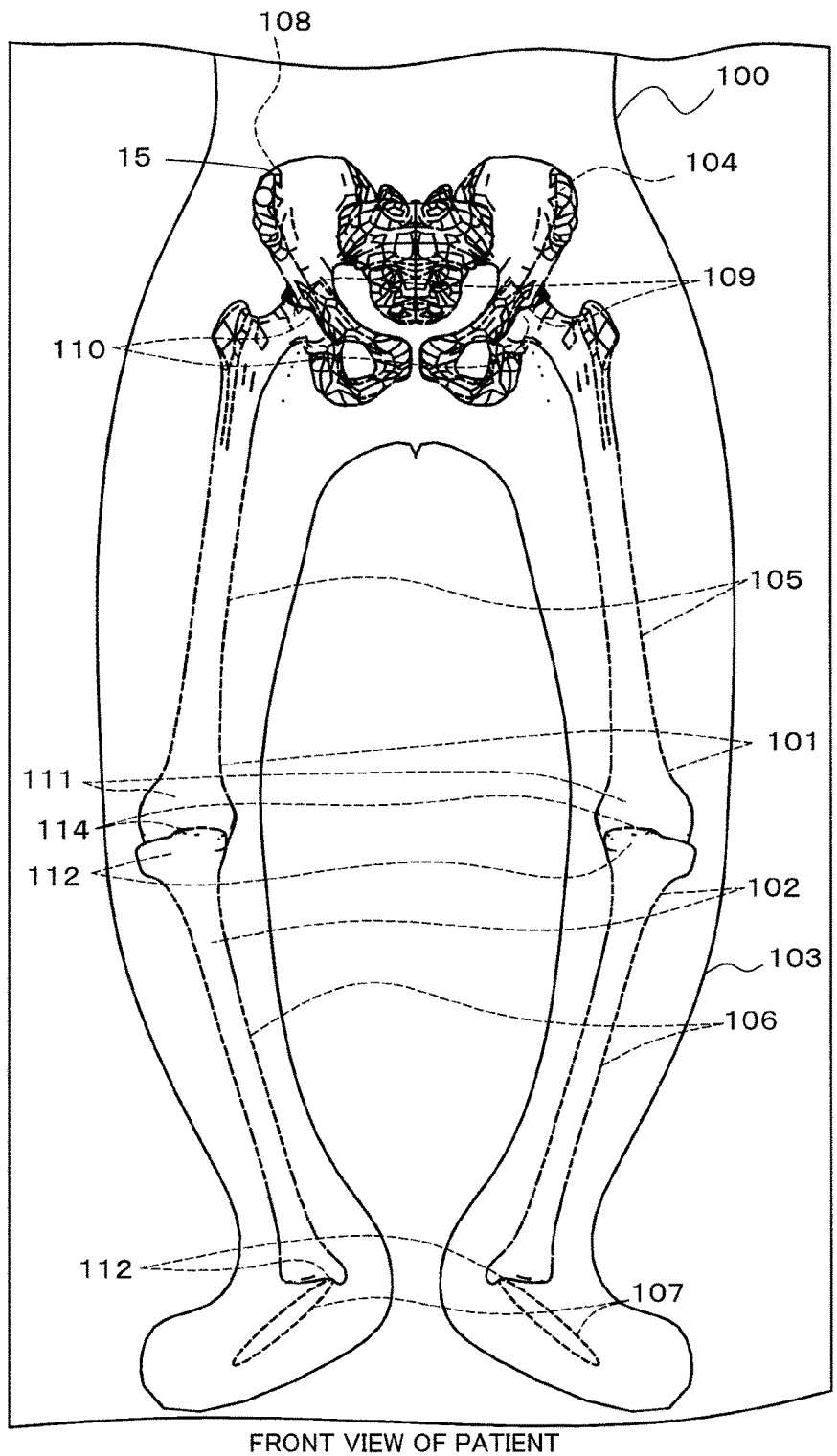
FIG. 2 is a front view of the patient.

FIG. 1 is a schematic diagram showing a surgical assistance apparatus 1 according to an embodiment of the present invention, a surgical table 2, and a patient 100. FIG. 2 is a front view of the patient. As shown in FIG. 1 and FIG. 2, the surgical assistance apparatus 1 is used when a surgeon performs a surgical operation on the patient 100, to visually guide the surgeon, regarding what kind of surgical operation is to be performed on the patient 100. More specifically, the surgical assistance apparatus 1 creates predetermined projection image data based on measurement data that has been obtained by measuring an affected part 101 of the patient 100.

The projection image specified by the projection image data is an image that is to be projected onto the surface of the patient 100 lying on the surgical table 2, specifically of the affected part 101 of the patient 100 and a portion around the affected part 101. This projection image includes a schematic image that shows the state that the affected part 101 is to be in after a surgical operation has started. The surgeon performs a surgical operation with reference to this projection image, and is thus able to more accurately check the state that the affected part 101 is to be in after the surgical operation has started, in advance of the surgical operation.

Figure 3A:
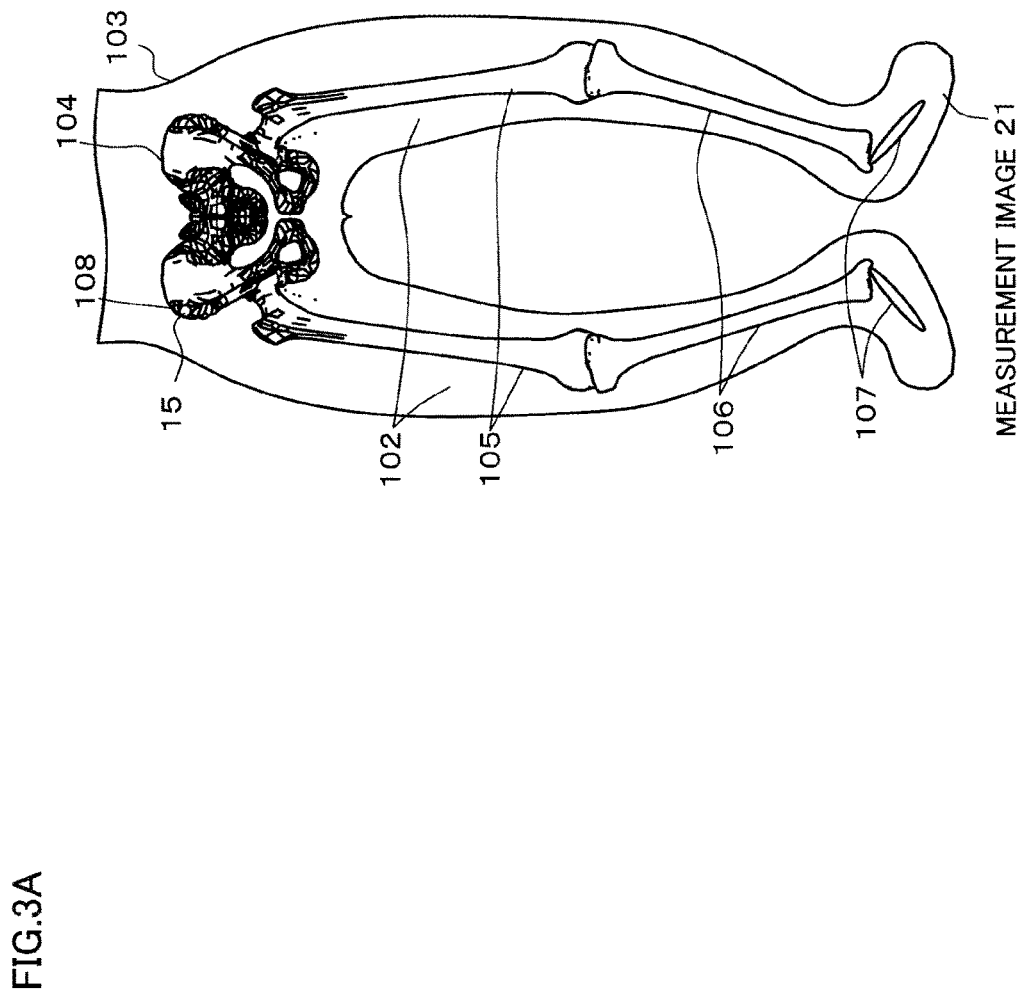
FIG. 3A is a diagram illustrating procedures for creating a projection image, and shows a measurement image.
Figure 3B:
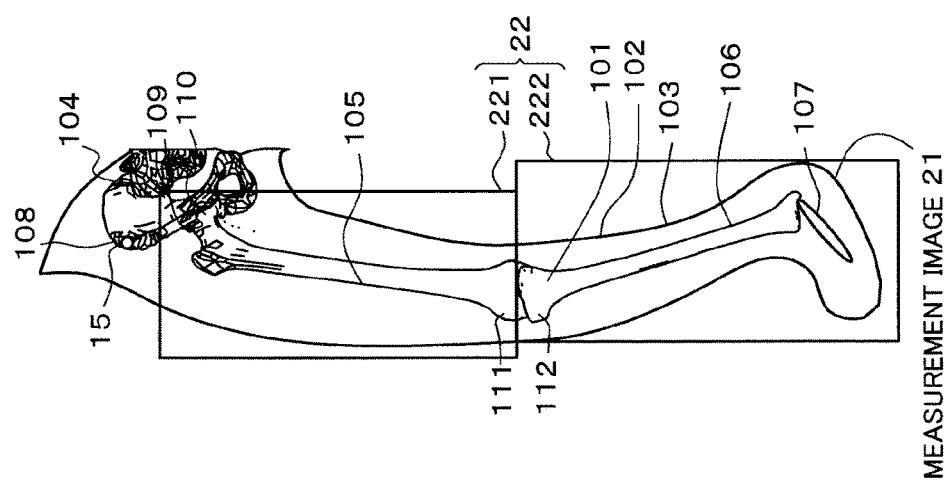
FIG. 3B is a diagram illustrating the procedures for creating a projection image, and shows a situation in which processing candidate regions are set based on the measurement image.
Figure 3C:
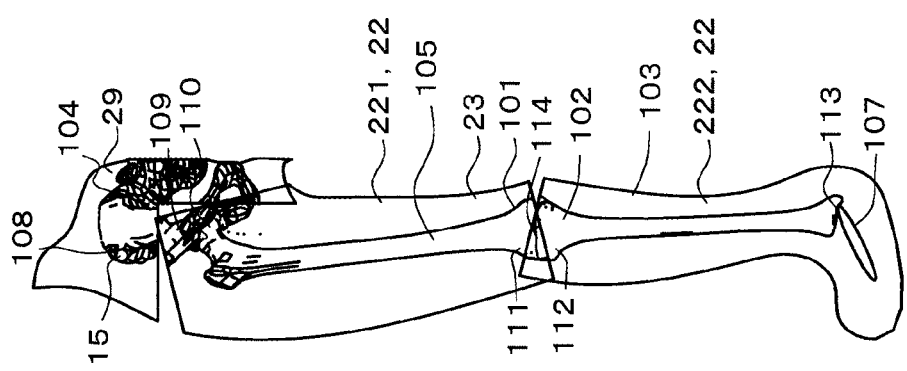
FIG. 3C is a diagram illustrating the procedures for creating a projection image, and shows a situation in which the processing candidate regions are subjected to rotation processing, and processing by which an image other than the processing candidate regions out of the measurement image is combined with the processed image is performed.
Figure 3D:
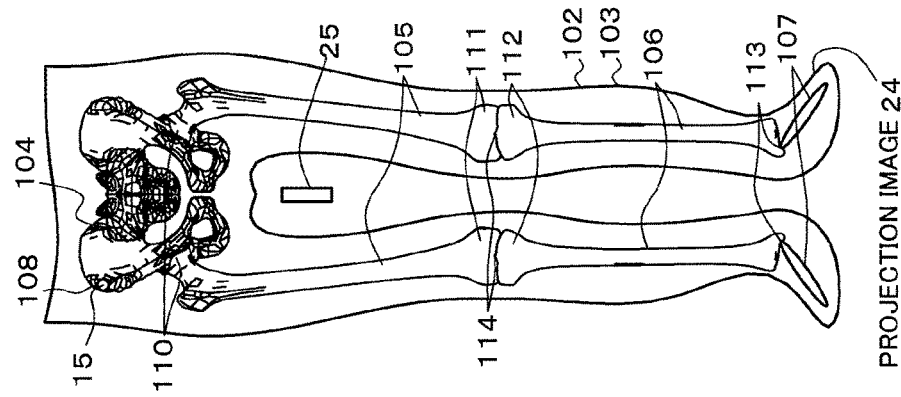
FIG. 3D is a diagram illustrating procedures for creating a projection image, and shows a situation in which the projection image is complete.

FIGS. 3A to 3D are diagrams illustrating procedures for creating a projection image 24. FIG. 3A shows a measurement image 21. FIG. 3B shows a situation in which processing candidate regions 22 out of the measurement image 21 are set. FIG. 3C shows a situation in which rotation processing is performed on the processing candidate regions 22, and an image 29 other than the processing candidate regions 22 out of the measurement image 21 is combined with a processed image 23. FIG. 3D shows a situation in which the projection image 24 is complete.

In the present embodiment, a description will be given of an example in which the surgeon performs a surgical operation on the patient 100 who suffers from knee osteoarthritis in legs 102 (the right leg and the left leg) with reference to FIGS. 1, 2, and 3A to 3D. In this case, the legs 102 of the patient 100 are severely bowed legs, for example. A knee joint operation is performed to restore the legs 102 to a straighter state.

The surgical assistance apparatus 1 includes an operation apparatus 3, a measurement data storage unit 4, an image processing unit 5, and an image display apparatus 6.

The operation apparatus 3, upon being operated by an operator such as a surgeon, outputs predetermined operation data (command signals) to the image processing unit 5 and the image display apparatus 6. The operation data is, for example, output to the image processing unit 5 in order to operate the measurement data. The operation data is also output to the image display apparatus 6 in order to cause the image display apparatus 6 to operate. The operation apparatus 3 includes a mouse and a keyboard, for example, and is connected to the image processing unit 5.

The measurement data storage unit 4 is provided as a portion that stores measurement data that has been obtained by measuring the affected part 101 of the patient 100, before a surgical operation is started. The measurement data storage unit 4 is, for example, a storage apparatus such as an HDD (Hard Disk Drive) or an SSD (Solid State Drive), or a storage medium such as an optical disc. The measurement data storage unit 4 is located outside the surgical field, for example.

The measurement data is data measured by using an image capturing apparatus, such as an X-ray image capturing apparatus, an MRI (Magnetic Resonance Imaging) apparatus, or a CT (Computed Tomography) apparatus (not shown) such as a three-dimensional CT apparatus. In the present embodiment, the measurement data is image data that specifies an image obtained by measuring the affected part 101 and a portion around the affected part 101. Note that the measurement data may be image data that specifies an image that shows essential positions such as the affected part 101 and so on in a simplified manner. This measurement data is processed by the image processing unit 5.

The image processing unit 5 is configured to create predetermined projection image data based on measurement data that has been obtained by measuring the affected part 101 of the patient 100, and thus create the projection image 24 as an image that is specified by the projection image data. This projection image 24 is an image that is to be projected onto the patient 100, and includes an image that shows the state that the affected part 101 is to be in after a surgical operation has started.

The image processing unit 5 is composed by using a computer that includes a CPU (Central Processing Unit), a GPU (Graphics Processing Unit), a RAM (Random Access Memory), and a ROM (Read Only Memory). The image processing unit 5 reads measurement data from the measurement data storage unit 4, and creates projection image data by applying predetermined image processing to this measurement data. The image processing unit 5 is placed outside the surgical field, for example.

The image processing unit 5 includes a measurement data obtaining unit 11, a region setting unit 12, and a processing unit 13.

The respective functions of the measurement data obtaining unit 11, the region setting unit 12, and the processing unit 13 are achieved by, for example, the CPU reading out and executing a program from a memory or a storage medium 500. This program can be installed from the outside of the surgical assistance apparatus 1. The program to be installed is distributed in the state of being contained (stored) in the storage medium 500, for example. Examples of the storage medium 500 include a DVD (Digital Versatile Disc) and a CD-ROM.

The measurement data obtaining unit 11 is provided as an interface unit that is to be connected to the measurement data storage unit 4. The measurement data obtaining unit 11 reads measurement data stored in the measurement data storage unit 4, via a read apparatus or the like, which is not shown.

The measurement image 21 is a front view of the patient 100, obtained by capturing an image of the lower body of the patient 100, using the above-described image capturing apparatus. This measurement image 21 includes, for example, images of a contour part 103, a pelvis 104, femurs 105, tibiae 106, and second metatarsal bones 107, of the lower body of the patient 100. As described above, the patient 100 suffers from knee osteoarthritis, and has bowed legs. Therefore, the knee joints of the legs 102 of the patient 100 are located at positions that are outward of the original positions of the knee joints in a medial-lateral direction (left-right direction).

The measurement image 21 further includes an image of an indicator 15 that is provided in a body part that serves as a referential body part of the patient 100 (an anterior superior iliac spine 108 in the present embodiment) when capturing the measurement image 21. The referential body part of the patient 100 is, for example, of parts of the patient 100, a part that is visible to the surgeon from the outside of the patient 100 while the surgeon is performing a surgical operation on the patient 100.

The anterior superior iliac spine 108 is a part of the patient 100 that is visible from the outside of the patient 100, and bulges underneath the skin of the patient 100 toward the outside of the patient 100. During a knee joint operation, the lower body of the patient 100 is covered by a surgical cover cloth (not shown). The anterior superior iliac spine 108 is visible to the surgeon, through the surgical cover cloth. The indicator 15 is a member whose image can be captured by the above-described image capturing apparatus, and is a pin member made of metal, for example.

As described above, in the present embodiment, the image processing unit 5 is configured to receive measurement data that specifies the measurement image 21 that includes an image of the femurs 105 and an image of the tibiae 106 of the patient 100. The measurement data obtained by the measurement data obtaining unit 11 is provided to the region setting unit 12.

The region setting unit 12 is configured to set the predetermined processing candidate regions 22 out of the measurement image 21. The processing candidate regions 22 are regions constituting parts of the measurement image 21, and are regions that are to be subjected to processing that is performed by the processing unit 13.

As clearly indicated in FIG. 3B, in the present embodiment, the region setting unit 12 sets, as the processing candidate regions 22 out of the measurement image 21, first processing candidate regions 221 that include images of the femurs 105, and second processing candidate regions 222 that include images of the tibiae 106.

In the present embodiment, the first processing candidate regions 221 include acetabulars 109, center points 110 of the capita of the femurs 105, and distal portions 111 of the femurs 105, of the legs 102 of the patient 100. Note that description of the right leg 102 is omitted from FIGS. 2B and 2C. In the present embodiment, the second processing candidate regions 222 include proximal portions 112 of the tibiae 106 and the second metatarsal bones 107 (the center points of the ankles), of the legs 102 of the patient 100.

The region setting unit 12 may be manually set by the surgeon operating the operation apparatus 3 in advance of a surgical operation, or automatically set by a predetermined image processing program. The image data of the measurement image 21 in which the processing candidate regions 22 have been set by the region setting unit 12 is output to the processing unit 13.

As shown in FIGS. 1, 2, 3C, and 3D, the processing unit 13 is configured to create the predetermined processed image 23 by applying predetermined processing to the processing candidate regions 22, and subsequently create the projection image 24 by performing processing to combine the processed image 23 with the image 29 other than the processing candidate regions 22 out of the measurement image 21. In the present embodiment, the processing unit 13 is configured to create the processed image 23 by applying processing including rotation processing to the processing candidate regions 22.

In the present embodiment, the processing unit 13 rotates each of the first processing candidate regions 221 of the right and left legs 102 by several number of degrees about the center point 110 of the corresponding caput in plan view. The processing unit 13 also rotates each of the second processing candidate regions 222 of the right and left legs 102 by several number of degrees about a center point 113 of the ankle related to the second metatarsal bone 107. As a result of such processing, the processing unit 13 creates the projection image 24 in which the center point 110 of the caput, a center point 114 of the knee joint, and the center point 113 of the ankle of each of the right and left legs 102 are aligned in a straight line.

The image processing unit 5 creates the projection image 24 such that the indicator 15 in the measurement image 21 is left in the image 21. In other words, the processing unit 13 generates the projection image 24 such that the projection image 24 includes the image of the indicator 15 provided on the anterior superior iliac spine 108 that serves as a referential body part of the patient 100 when the measurement image 21 is to be captured. Also, the image processing unit 5 generates the projection image 24 such that a scale 25 is displayed on the projection image 24. This scale 25 is used as a reference for a scale adjustment when the projection image 24 is to be projected onto the surface of the patient 100.

For example, the size of each part in the projection image 24 matches the actual size of the patient 100 when the projection image 24 is projected by the image display apparatus 6 such that the scale 25 has a length of 10 cm. The scale 25 may be projected onto the patient 100, or onto the surgical table 2. The processing unit 13 outputs projection image data that specifies the projection image 24, to the image display apparatus 6.

The image display apparatus 6 is, for example, a projector apparatus, and is configured to display the projection image 24 by being supplied with the projection image data. The image display apparatus 6 is located inside the surgical field. The image display apparatus 6 has a lens 26, and this lens 26 faces the surgical table 2. The image display apparatus 6 is configured such that the position of the image display apparatus 6 relative to the surgical table 2 can be manually changed, or can be changed by a driving apparatus, which is not shown. With this configuration, it is possible to adjust the position of the projection image 24 emitted from the lens 26, relative to the patient 100.

Figure 4:
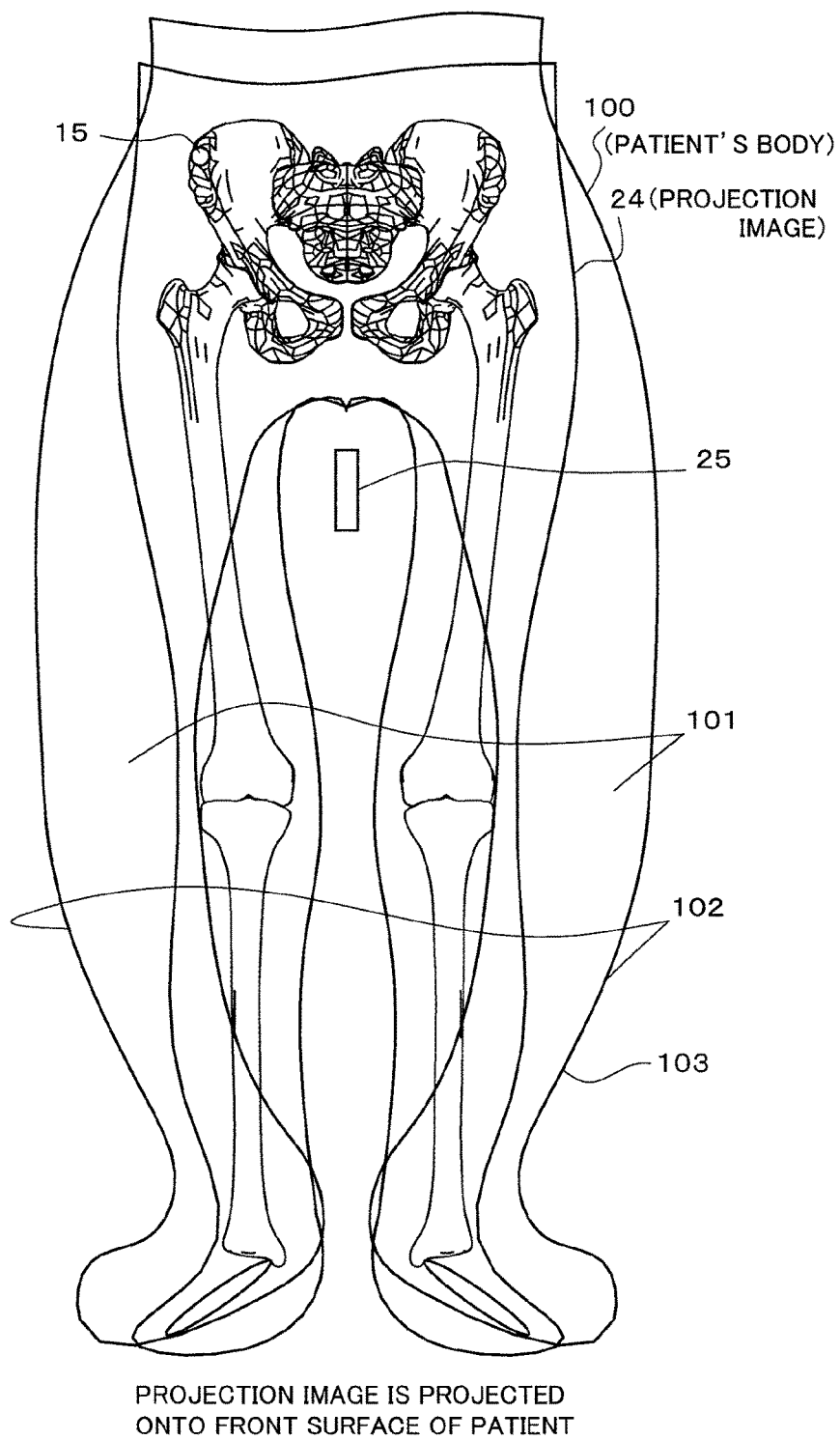
FIG. 4 is a schematic front view showing a situation in which the projection image is projected onto a patient.

For example, when a surgical operation is to be started, the projection image 24 is projected onto the patient 100 from the image display apparatus 6, and the projection image 24 is projected onto surface of the legs 102 of the patient 100 as shown in FIG. 4. FIG. 4 is a schematic front view showing a situation in which the projection image 24 is projected onto the patient 100.

At this time, the projection image 24 is located such that the image of the indicator 15 in the projection image 24 overlays the indicator 15 provided on the anterior superior iliac spine 108, which is the referential body part of the patient 100. Also, the lens 26 is operated so that the scale 25 has a predetermined length, and thus the sizes of the parts in the projection image 24 match the sizes of the parts of the patient 100. The above-described configuration allows the surgeon to visually check the postoperative state of the affected part 101 of the patient 100 in advance of starting a surgical operation on the patient 100.

Figure 5:
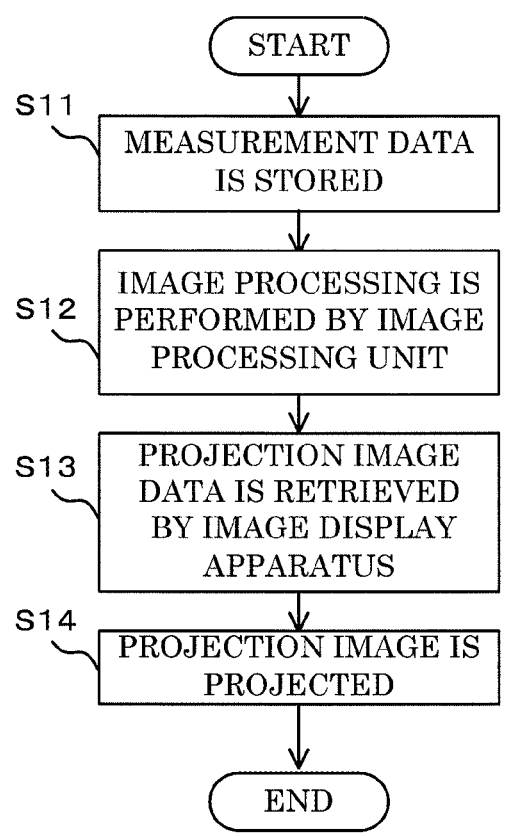
FIG. 5 is a flowchart illustrating an example of processing that is performed by the surgical assistance apparatus.

Next, an example of processing that is performed by the surgical assistance apparatus 1 will be described. FIG. 5 is a flowchart illustrating an example of processing that is performed by the surgical assistance apparatus 1. In the following description, when a description is given with reference to a flowchart, diagrams other than the flowchart are also referred to as appropriate.

As shown in FIG. 5, the operation of the surgical assistance apparatus 1 is started upon the surgeon operating the operation apparatus 3. When the projection image 24 is to be created by the surgical assistance apparatus 1, first, an image of the lower part of the patient 100 including the affected part 101 is captured by using the image capturing apparatus, and thus measurement data (the measurement image 21) is obtained. Then, the measurement data is stored in the measurement data storage unit 4 (step S11).

Next, the image processing unit 5 performs image processing based on the measurement data (the measurement image 21) (step S12). Specifically, the region setting unit 12 sets the processing candidate regions 22. Subsequently, the processing unit 13 applies rotation processing to the processing candidate regions 22. Consequently, the projection image 24 (the projection image data) in which the images of the center points 110 of the capita, the center points 114 of the knee joints, and the center points 113 of the ankles are aligned in straight lines is created.

Next, the image display apparatus 6 retrieves the projection image data from the image processing unit 5 (step S13). Then, the image display apparatus 6 projects the projection image 24 specified by the projection image data onto the patient 100 on the surgical table 2 (step S14).

Program

A program according to the present embodiment may be any program as long as it is a program that causes a computer to execute processing that is to be performed by the image processing unit 5. The image processing unit 5 according to the present embodiment can be realized by installing this program to a computer and executing the program. In this case, the CPU (Central Processing Unit) of the computer functions as the measurement data obtaining unit 11, the region setting unit 12, and the processing unit 13 and performs processing. Note that the image processing unit 5 may be realized by software and hardware cooperating with each other, or by hardware. Also, the program according to the present embodiment may be distributed in the state of being stored in the storage medium 500 such as a DVD (Digital Versatile Disc), or distributed via a wired or wireless communication network.

As described above, with the surgical assistance apparatus 1 according to the present embodiment, the projection image 24 to be projected onto the patient 100 includes an image (a guide image) that shows the state of the affected part 101 at the time after a surgical operation on the affected part 101 has started. Therefore, due to this projection image 24 being projected onto the patient 100, the surgeon can more accurately check the shape that the affected part 101 will take on after the surgical operation has started, in advance of the surgical operation. Consequently, the surgeon can more accurately perform a surgical operation on the patient 100. Thus, it is possible to realize the surgical assistance apparatus 1 that allows the surgeon to more accurately check the state that the affected part 101 is to be in after the surgical operation has started, in advance of the surgical operation.

Also, in the surgical assistance apparatus 1, the region setting unit 12 is configured to set the predetermined processing candidate regions 22 (221 and 222) out of the measurement image 21. Then, the processing unit 13 creates the processed image 23 by applying processing to the processing candidate regions 22, and subsequently creates the projection image 24 by performing processing to combine the processed image 23 with the image 29 other than the processing candidate regions 22 out of the measurement image 21. With this configuration, the projection image 24 shows how the affected part 101 of the patient 100 and a portion around the affected part 101 are to be coupled to each other. Therefore, the surgeon can more accurately check the state that the patient 100 is to be in after a surgical operation has started, in advance of the operation, by referring to the projection image 24 projected onto the patient 100.

Also, in the surgical assistance apparatus 1, the region setting unit 12 is configured to set, as the processing candidate regions 22, the first processing candidate regions 221 that include images of the femurs 105 and the second processing candidate regions 222 that include images of the tibiae 106. Then, the processing unit 13 creates the processed image 23 by applying processing including rotation processing to the processing candidate regions 22. With this configuration, when performing a surgical operation on the patient 100 suffering from knee osteoarthritis, it is possible to realize the projection image 24 that shows the state that the patient 100 is to be in after the surgical operation has started. Consequently, the surgeon can more accurately perform a surgical operation for knee osteoarthritis.

Also, in the surgical assistance apparatus 1, the processing unit 13 creates the projection image 24 in which the center points 110 of the capita, the center points 114 of the knee joints, and the center points 113 of the ankles in the measurement image 21 are aligned in straight lines. With this configuration, when performing a surgical operation for knee osteoarthritis, the surgeon can more accurately check a targeted positional state that the affected part 101 should take on, in advance of the surgical operation. In particular, the surgeon can visually check the positions of the center points 110 of the capita that cannot be directly seen while the surgeon is performing the surgical operation.

Also, in the surgical assistance apparatus 1, the processing unit 13 generates the projection image 24 such that the projection image 24 includes the image of the indicator 15 provided on a part that serves as a referential body part of the patient 100 when the measurement image 21 is to be captured. With this configuration, it is possible to adjust the position of each part in the projection image 24 to the actual position at which the part will be located after a surgical operation on the patient 100 has started, by overlaying the image of the indicator 15, included in the projection image 24, upon the actual indicator 15 provided on the anterior superior iliac spine 108, which is the referential body part of the patient 100. Consequently, the surgeon can more accurately check how the affected part 101 should be treated after the surgical operation has started.

Also, in the surgical assistance apparatus 1, the image processing unit 5 is configured to create a postoperative image of the affected part 101 as the projection image 24. With this configuration, the projection image 24 includes a postoperative image of the affected part 101, and therefore the surgeon can more accurately check the postoperative state of the affected part 101.

The surgical assistance apparatus 1 further includes the image processing unit 5, the operation apparatus 3, and the image display apparatus 6. With this configuration, the surgical assistance apparatus 1 can create a projection image 24 that is desired by the surgeon upon, for example, the surgeon operating the operation apparatus 3. Also, this projection image 24 can be projected onto the patient 100 by using the image display apparatus 6.

Also, the surgical assistance apparatus 1 eliminates the necessity for a robot apparatus that assists a surgeon in performing a surgical operation, and for PSIs (Patient Specific Instruments) for individual patients, and thus the surgical assistance apparatus 1 can further reduce the cost of a surgical operation.

Figure 6A:
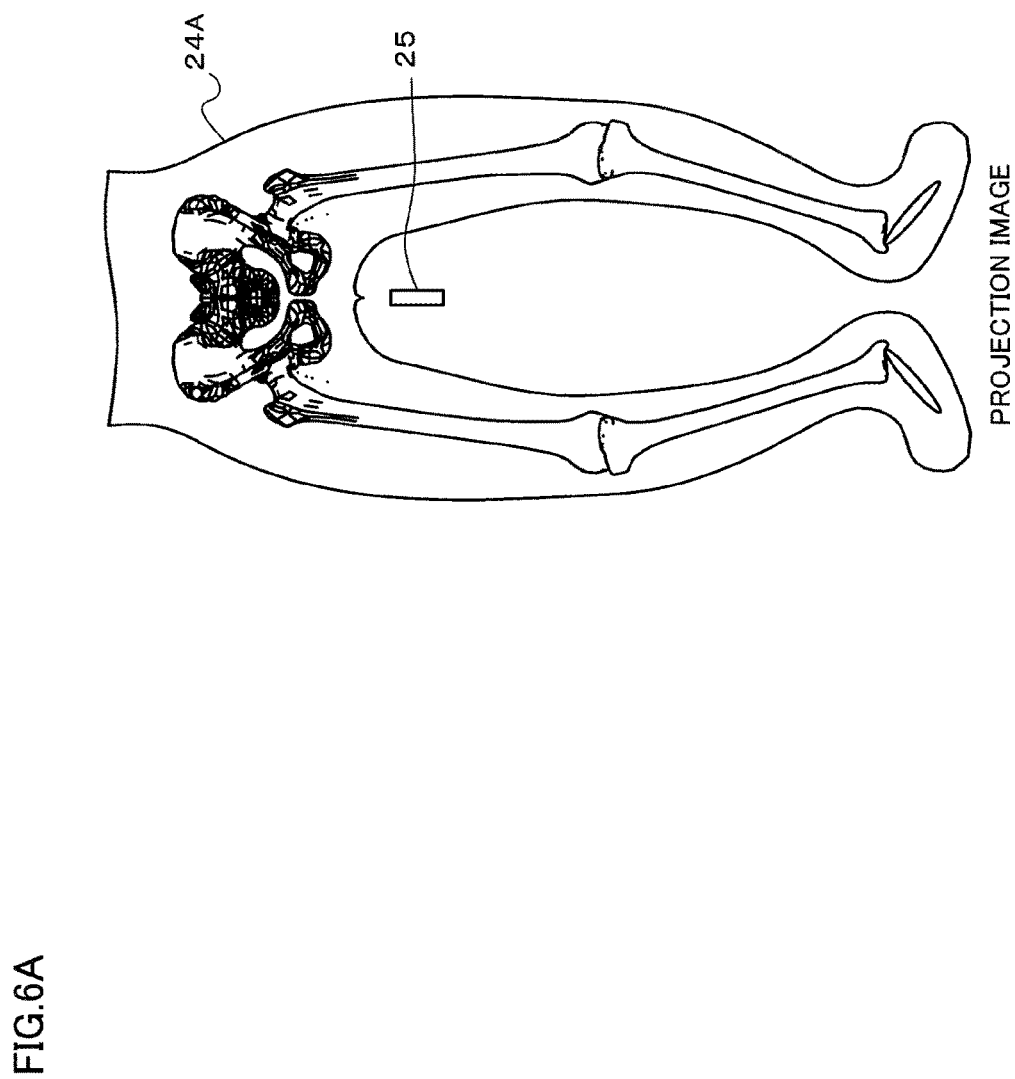
FIG. 6A is a diagram illustrating a configuration for creating a preoperative image of the patient as the projection image.
Figure 6B:
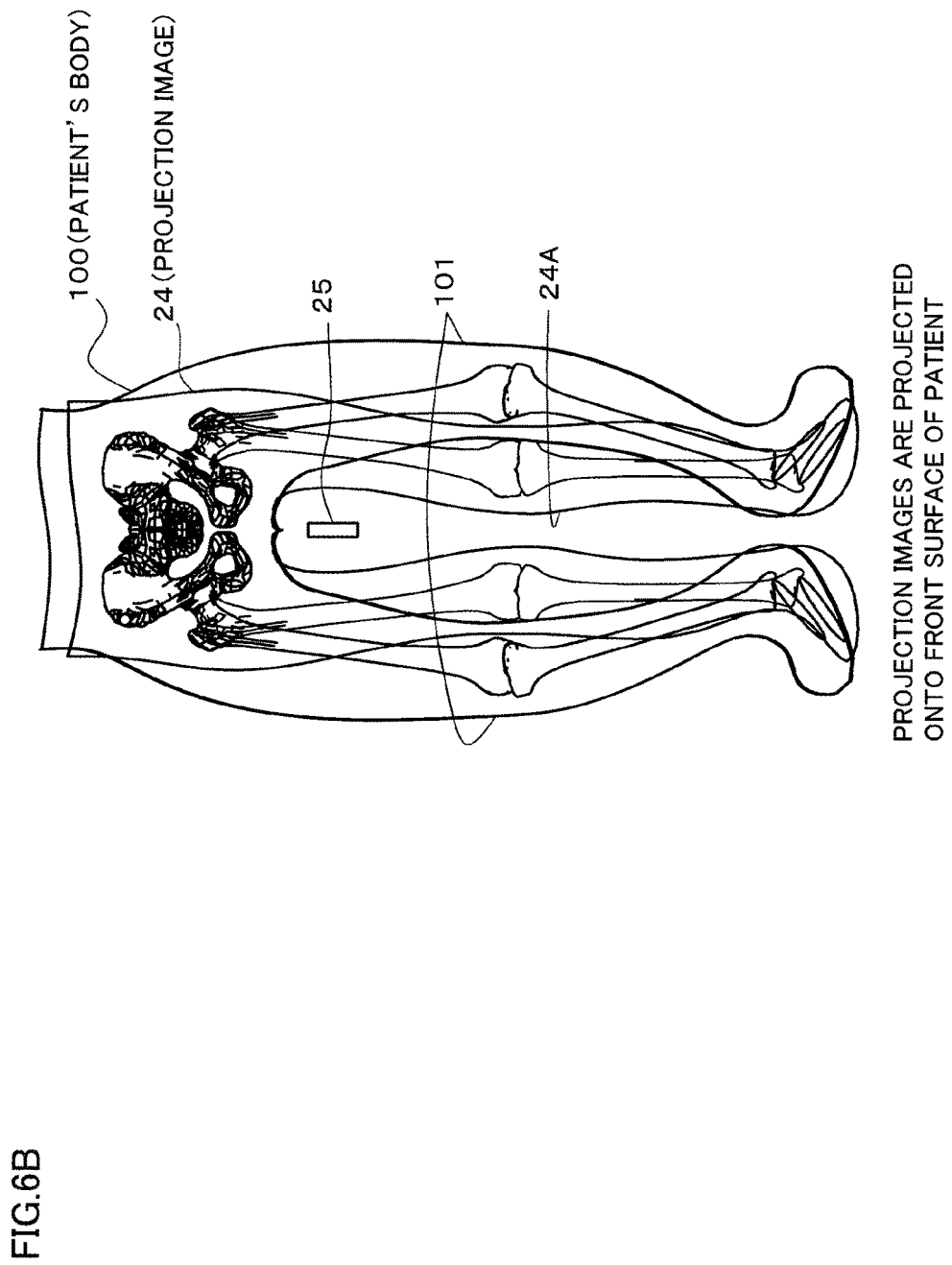
FIG. 6B is a diagram showing a situation in which the projection image is projected onto an affected part of the patient.

In the embodiment above, a mode in which a postoperative image of the affected part 101 is created as the projection image 24 is described as an example. However, the projection image 24 is not limited to this example. For example, as shown in FIG. 6A, a preoperative image of the patient 100 may be created as a projection image 24A. If this is the case, the image processing unit 5 creates an image of the affected part 101 for which the measurement data (measurement image 21) is yet to be processed, as the projection image 24A. In other words, the projection image 24A is the measurement image 21 in itself. If this is the case, as shown in FIG. 6B, the projection image 24 and the projection image 24A are selectively or simultaneously displayed on the affected part 101 of the patient 100 and a portion around the affected part 101.

With this configuration, due to the projection images 24 and 24A being projected onto the patient, the surgeon can check both a preoperative state and a state after the surgical operation has started. Consequently, the surgeon can more accurately and easily perform a surgical operation.

Figure 7A:
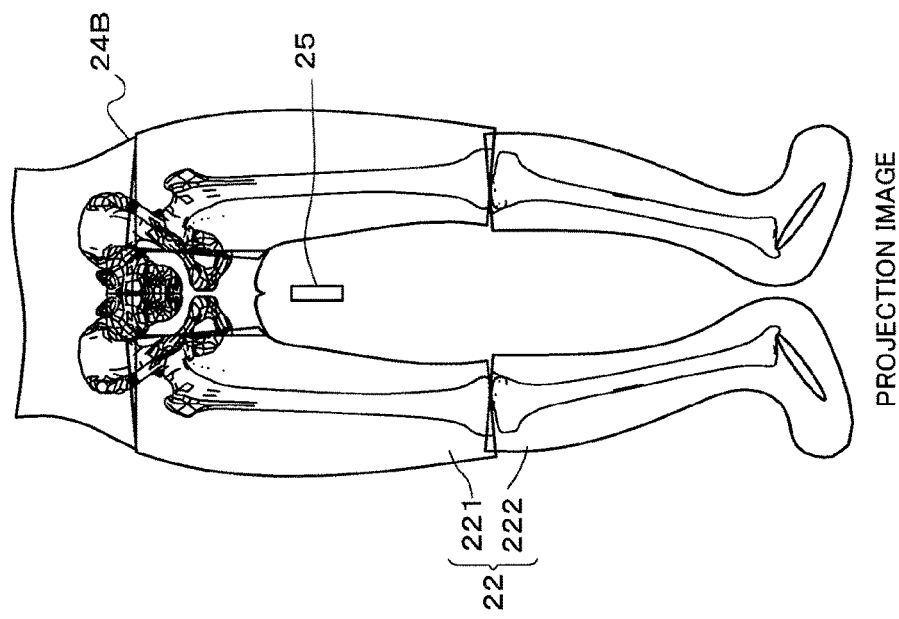
FIG. 7A is a diagram illustrating a configuration for creating an intraoperative image of the patient as the projection image.
Figure 7B:
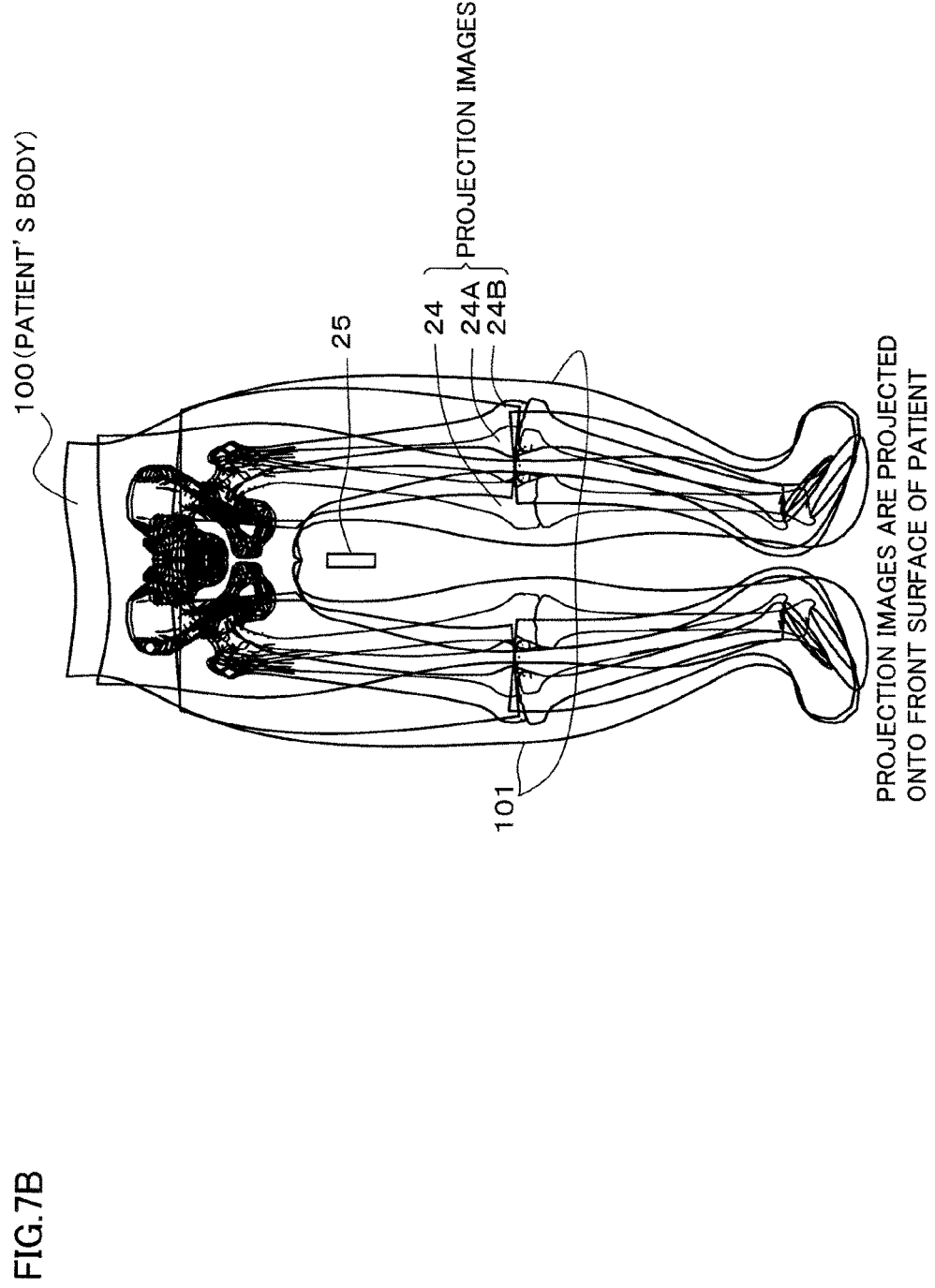
FIG. 7B is a diagram showing a situation in which the projection image is projected onto the affected part of the patient.

Also, as shown in FIG. 7A, an intraoperative image of the patient 100 may be created as a projection image 24B. In this case, the projection image 24B is created by performing processing that is the same as the processing for creating the projection image 24 except that the respective rotational angles of the first processing candidate region 221 and the second processing candidate region 222 are set to be values that are smaller than the corresponding rotational angles in the case of creating the projection image 24. If this is the case, as shown in FIG. 7B, the projection image 24A, the projection image 24B, and the projection image 24 are selectively or simultaneously displayed on the affected part 101 of the patient 100 and a portion around the affected part 101.

With this configuration, the projection image 24B includes an intraoperative image of the affected part 101, and therefore the surgeon can more accurately check the intraoperative state of the affected part 101. Also, the projection image 24 includes a postoperative image of the affected part 101, and therefore the surgeon can more accurately check the postoperative state of the affected part 101.

Note that, if the projection image 24B showing the intraoperative state of the patient 100 is formed, the projection image 24 showing the postoperative state of the patient 100 is not required to be created.

Figure 8A:
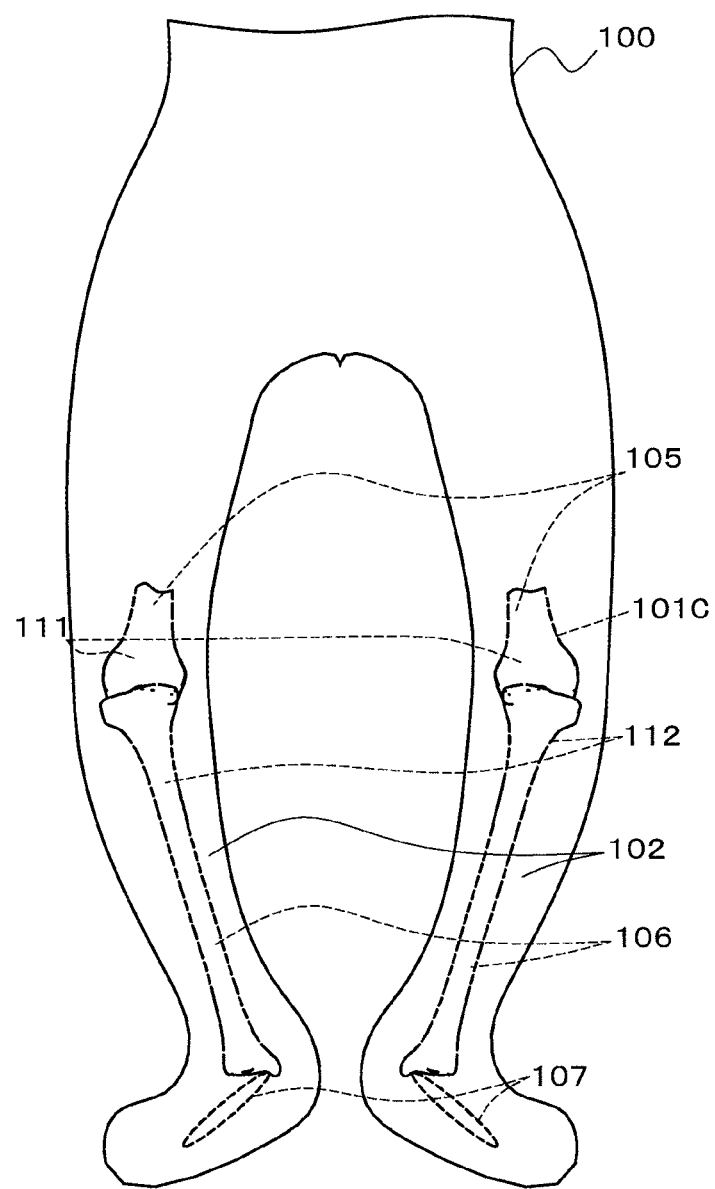
FIG. 8A is a front view of the patient.
Figure 8B:
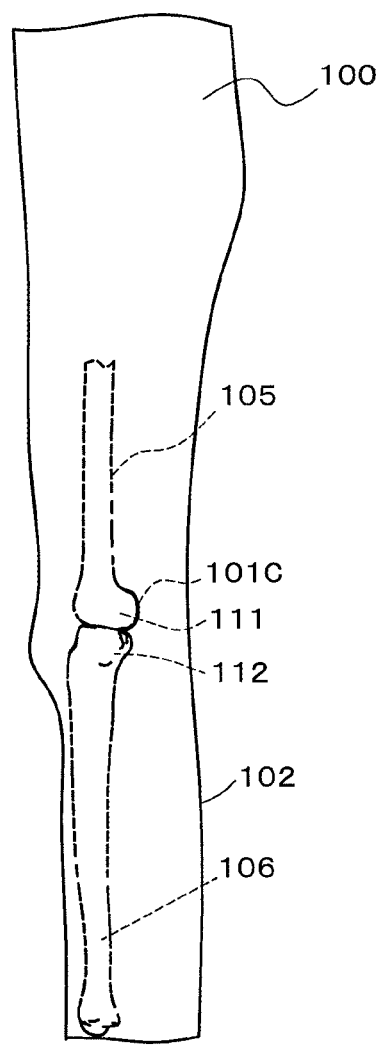
FIG. 8B is a side view of the patient.
Figure 9A:
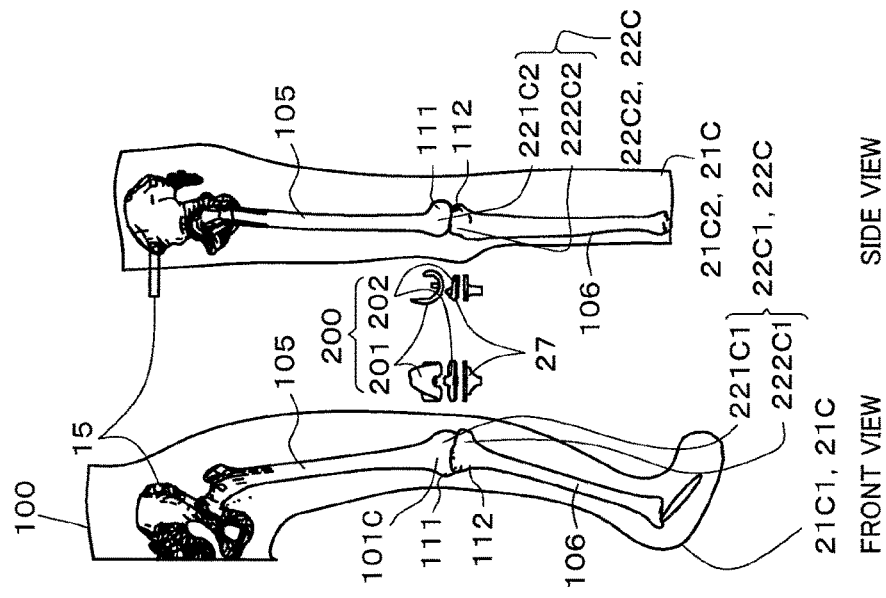
FIG. 9A shows a front view and a side view illustrating image processing that is performed by using the surgical assistance apparatus, and shows a measurement image and an insertion image.
Figure 9B:
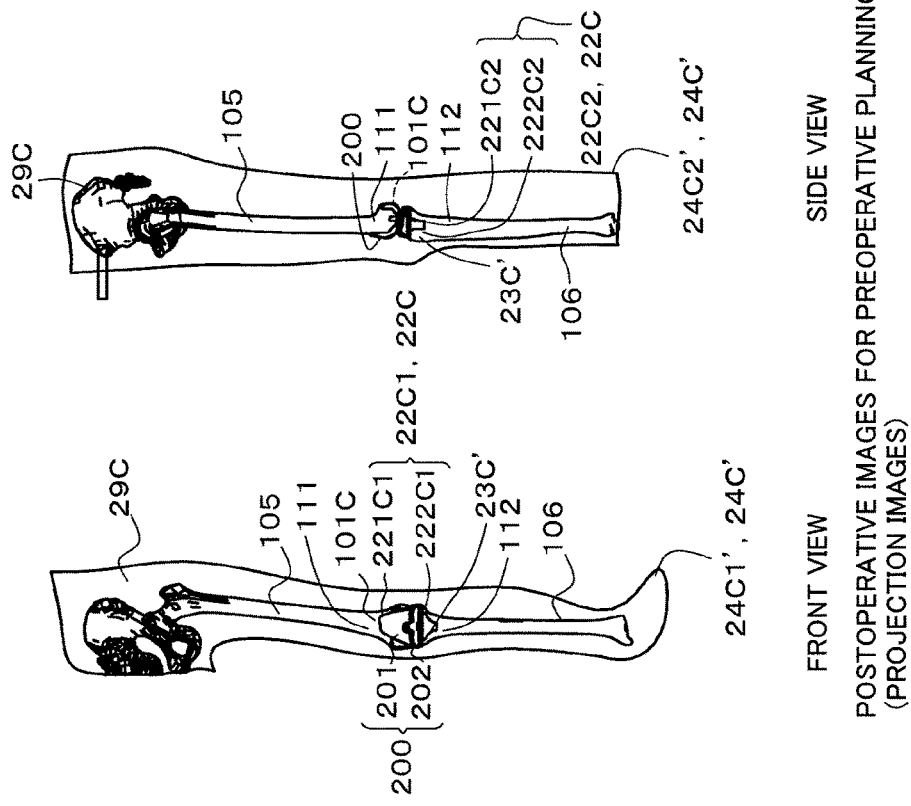
FIG. 9B shows a front view and a side view illustrating image processing that is performed by using the surgical assistance apparatus, and shows a postoperative projection image, which is used for preoperative planning.
Figure 10A:
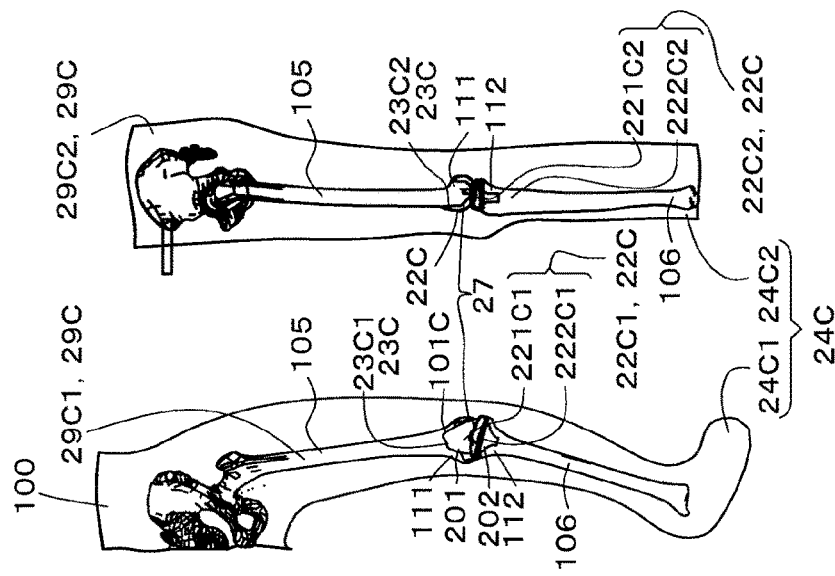
FIG. 10A shows a front view and a side view illustrating image processing that is performed by using the surgical assistance apparatus, and shows an intraoperative projection image.
Figure 10B:
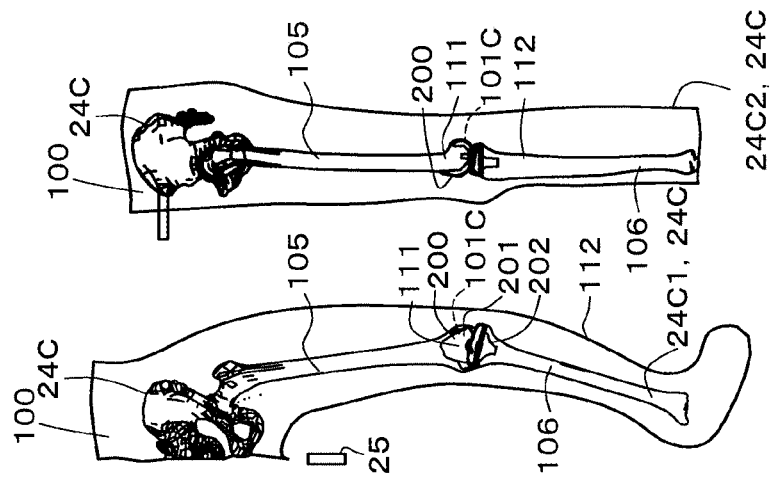
FIG. 10B shows a front view and a side view illustrating image processing that is performed by using the surgical assistance apparatus, and shows a situation in which an intraoperative projection image is projected onto the patient.

The surgical assistance apparatus 1 may be applied to a total knee replacement, by which the knee joint of the patient 100 is replaced with an artificial knee joint implant 200. FIG. 8A is a front view of the patient 100, and FIG. 8B is a side view of the patient 100. FIGS. 9 to 11 are front views and side views illustrating image processing that is performed by using the surgical assistance apparatus 1. FIG. 9A shows measurement images 21C and insertion images 27, FIG. 9B shows postoperative projection images 24C' used for preoperative planning, FIG. 10A shows intraoperative projection images 24C, FIG. 10B shows a situation where the projection images 24C are projected onto a patient, and FIG. 11 shows a situation where the projection images 24C and 24C' are projected onto the patient. Note that, in FIGS. 9A to 11, description of the right side part of the patient 100 is omitted.

As shown in FIGS. 1, 8, 9A, 9B, 10A, and 10B, the artificial knee joint implant 200 includes a femur component 201 that is fixed to the distal portion 111 of the femur 105, and a tibia component 202 that is fixed to the proximal portion 112 of the tibia 106. A configuration is adopted in which the femur component 201 and the tibia component 202 slide relative to each other when the knee is bent.

In the following, differences from the above-described embodiment will be mainly described. The similar configurations will be denoted by the similar reference numerals, and descriptions thereof will be omitted.

In the present embodiment, the measurement data storage unit 4 stores measurement data that has been obtained by measuring an affected part 101C of the patient 100, before a surgical operation is started. In the present embodiment, the measurement data is image data that has been obtained by capturing an image of the left leg 102 of the patient 100, including the affected part 101C, by using the above-described image capturing apparatus. The measurement images 21C specified by this measurement data include a measurement image 21C1 captured from the front side of the patient 100 and a measurement image 21C2 captured from the left side of the patient 100.

The image processing unit 5 creates intraoperative images of the affected part 101C as the projection images 24C (24C1 and 24C2). The image processing unit 5 also creates postoperative images of the affected part 101C as the projection images 24C' (24C1' and 24C2'). The projection images 24C' are images showing a postoperative state used for preoperative planning. Each of the projection images 24C and 24C' is an image that includes an image of the artificial knee joint implant 200 that is to be placed in the affected part 101C.

Specifically, in the present embodiment, the image processing unit 5 is configured to receive measurement data that specifies the measurement images 21C that include images of the femur 105 and images of the tibia 106 of the patient 100. The measurement data that has been obtained by the measurement data obtaining unit 11 is provided to the region setting unit 12.

The region setting unit 12 is configured to set predetermined processing candidate regions 22C out of the measurement images 21C.

In the present embodiment, the region setting unit 12 sets, as the processing candidate regions 22C out of the measurement images 21C, first processing candidate regions 221C1 and 221C2 that include images of the distal portion 111 of the femur 105 and a portion around the distal portion 111, and second processing candidate regions 222C1 and 222C2 that include images of the proximal portion 112 of the tibia 106 and a portion around the proximal portion 112. The image data of the measurement images 21C in which the processing candidate regions 22C have been set by the region setting unit 12 is output to the processing unit 13.

The processing unit 13 is configured to create predetermined processed images 23C' by applying predetermined processing to the processing candidate regions 22C, and subsequently create the projection images 24C' by performing processing to combine the processed images 23C' with the images 29C other than the processing candidate regions 22C out of the measurement images 21C. In the present embodiment, the processing unit 13 is configured to create the processed images 23C' by applying processing including rotation processing and image addition processing to the processing candidate regions 22C.

More specifically, as clearly shown in FIG. 9B, the processing unit 13 rotates each of the first processing candidate regions 221C1 and 221C2 (the femur 105) and the second processing candidate regions 222C1 and 222C2 (the tibia 106) by a predetermined number of degrees in plan view. The processing unit 13 overlays the corresponding front image and side image of the insertion images 27 of the femur component 201 onto the first processing candidate regions 221C1 and 221C2. The processing unit 13 also overlays the corresponding front image and side image of the insertion images 27 of the tibia component 202 upon the second processing candidate regions 222C1 and 222C2.

As a result of such processing, the processing unit 13 creates the projection images 24C' (24C1' and 24C2') showing a postoperative state in which the femur component 201 is attached to the distal portion 111 of the femur 105 of the left leg 102, and the tibia component 202 is attached to the proximal portion 112 of the tibia 106 of the left leg 102.

The processing unit 13 is also configured to create predetermined processed images 23C by applying predetermined processing to the processing candidate regions 22C, and subsequently create the projection images 24C by performing processing to combine the processed images 23C with the images 29C other than the processing candidate regions 22C out of the measurement images 21C. In the present embodiment, the processing unit 13 is configured to create the processed images 23C by applying processing including image addition processing to the processing candidate regions 22C.

More specifically, as clearly shown in FIG. 10A, the processing unit 13 overlays the corresponding front image and side image of the insertion images 27 of the femur component 201 upon the first processing candidate regions 221C1 and 221C2. The processing unit 13 also overlays the corresponding front image and side image of the insertion images 27 of the tibia component 202 upon the second processing candidate regions 222C1 and 222C2. In the projection images 24C showing an intraoperative state, the angles at which the femur component 201 and the tibia component 202 are placed are determined based on the projection images 24C' used for preoperative planning.

As a result of such processing, the processing unit 13 creates the projection images 24C (24C1 and 24C2) showing an intraoperative state in which the femur component 201 is attached to the distal portion 111 of the femur 105 of the left leg 102, and the tibia component 202 is attached to the proximal portion 112 of the tibia 106 of the left leg 102. Then, as shown in FIG. 10B, the projection image 24C1 is projected onto the front surface of the left leg 102 of the patient 100, and the projection image 24 C2 is projected onto the side surface of the left leg 102 of the patient 100. Note that, as shown in FIG. 11, the projection images 24C showing an intraoperative state and the projection images 24C' showing a postoperative state may be selectively or simultaneously projected onto the patient 100.

In this case, an example of processing related to the surgical assistance apparatus 1 is performed as shown in FIGS. 1, 5, 8, 9A, 9B, 10A, 10B, and 11. Specifically, in the surgical assistance apparatus 1, when the projection images 24C and 24C' are to be created, first, measurement data (the measurement images 21C) is obtained by capturing images of the lower part of the patient 100 including the affected part 101C, using the image capturing apparatus, and then this measurement data is stored in the measurement data storage unit 4 (step S11).

Next, the image processing unit 5 performs image processing based on the measurement data (the measurement images 21C) (step S12). Specifically, the region setting unit 12 sets the processing candidate regions 22C. Subsequently, the processing unit 13 rotates the processing candidate regions 22C, and overlays images of the femur component 201 and images of the tibia component 202 (the insertion images 27) on the processing candidate regions 22C. Thus, the projection images 24C' (the projection image data) are created. Also, the processing unit 13 overlays the images of the femur component 201 and the images of the tibia component 202 (the insertion images 27) upon the processing candidate regions 22C. Thus, the projection images 24C (the projection image data) are created.

Next, the image display apparatus 6 retrieves the projection image data from the image processing unit 5 (step S13). Then, the image display apparatus 6 projects the projection images 24C and 24C' specified by the projection image data onto the patient 100 on the surgical table 2 (step S14).

As described above, in the case where the surgical assistance apparatus 1 is used for a total knee replacement, the image processing unit 5 creates images that include images (the insertion images 27) of the artificial knee joint implant 200 that is to be placed in the affected part 101C, as the projection images 24C and 24C'. With this configuration, when performing a total knee replacement, the surgeon can more accurately check the state that the affected part 101C is to be in after a surgical operation has started, in advance of the surgical operation.

Figure 12:
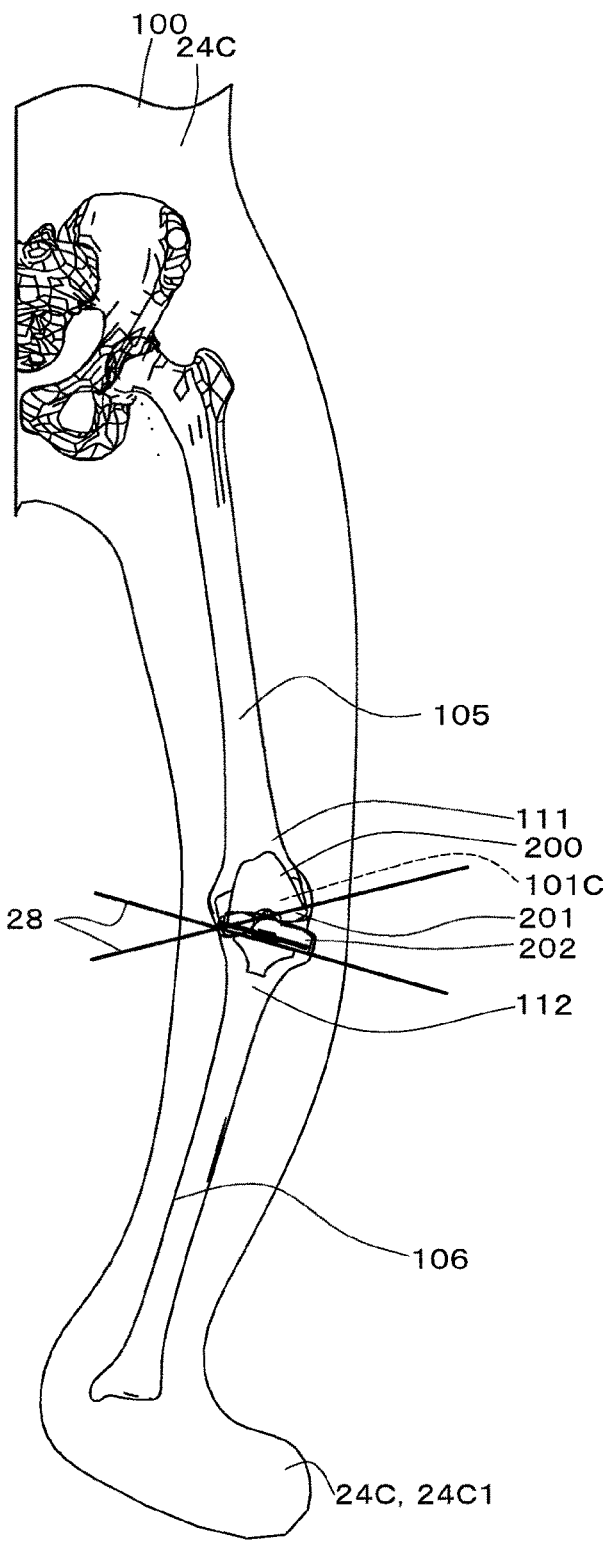
FIG. 12 is a front view showing a situation in which osteotomy lines are included in the projection image.

Note that, as shown in FIG. 12, the projection image 24C may include osteotomy lines 28. The osteotomy lines 28 are straight lines that are displayed on the distal portion 111 of the femur 105 and the proximal portion 112 of the tibia 106 in the projection image 24C. When performing the task of osteotomy that is required for placing the femur component 201 and the tibia component 202, the surgeon can perform osteotomy on the femur 105 and the tibia 106 of the patient 100 while referring to the osteotomy lines 28.

With this configuration, the projection image 24C includes an intraoperative image (the osteotomy lines 28) of the affected part 101C, and therefore the surgeon can more accurately check the intraoperative state of the affected part 101C. Also, the projection image 24C includes a postoperative image of the affected part 101C, and therefore the surgeon can more accurately check the postoperative state of the affected part 101C.

Note that the surgical assistance apparatus 1 can be used for the placement of an implant other than an artificial knee joint implant.

Figure 13:
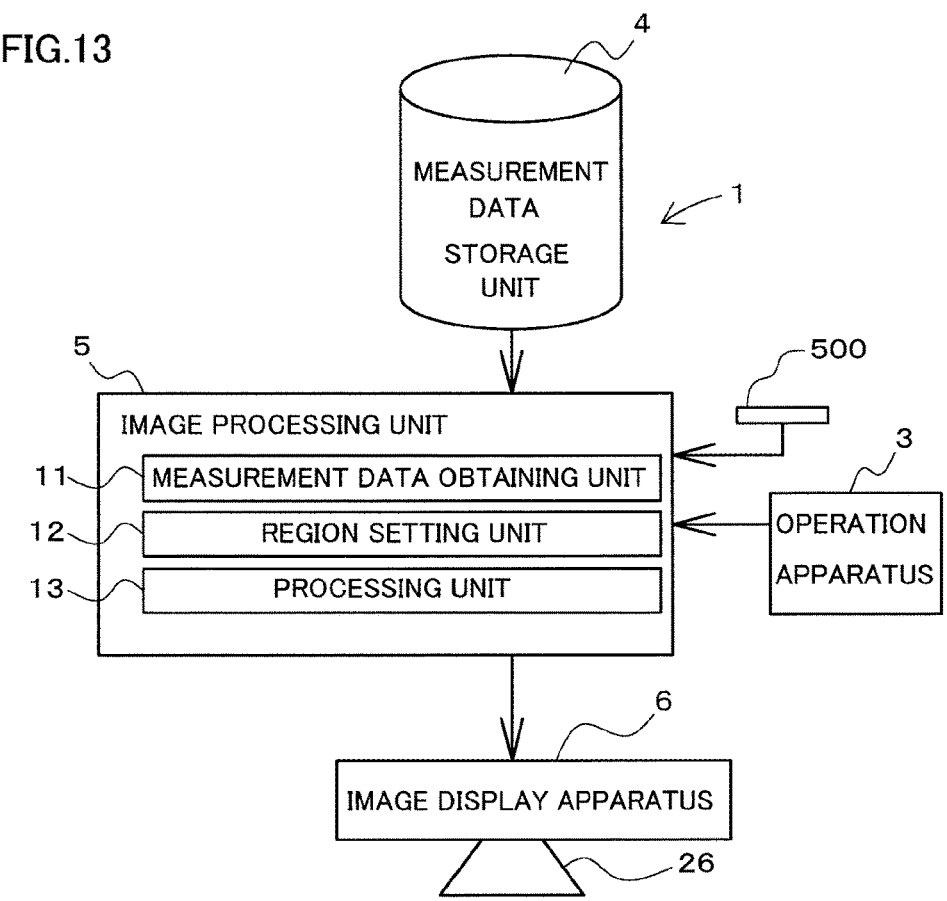
FIG. 13 is a schematic diagram showing the surgical assistance apparatus and the patient.

As shown in FIG. 13, the surgical assistance apparatus 1 may be used when a gastrectomy, which is removal of at least a part of the stomach, is performed on the patient 100 on the surgical table 2. FIG. 13 is a schematic diagram showing the surgical assistance apparatus 1 and the patient 100.

FIGS. 14A to 14E are diagrams illustrating image processing that is performed by using the surgical assistance apparatus 1. As shown in FIGS. 13 and 14A to 14E, in the present embodiment, the measurement data storage unit 4 stores measurement data that has been obtained by measuring an affected part 101D of the patient 100, before a surgical operation is started. In the present embodiment, the measurement data is image data that has been obtained by capturing an image of a portion around a stomach 115 of the patient 100, including the affected part 101D, from the front side of the patient 100, by using the above-described image capturing apparatus.

The image processing unit 5 creates a postoperative image of the affected part 101D as a projection image 24D. Specifically, in the present embodiment, the image processing unit 5 is configured to receive measurement data that specifies the measurement image 21 that includes an image of the stomach 115 of the patient 100.

The region setting unit 12 is configured to set a predetermined processing candidate region 22D out of the measurement image 21.

Figure 14A:
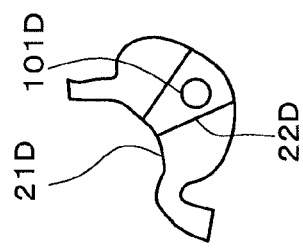
FIG. 14A is a diagram illustrating image processing that is performed by using the surgical assistance apparatus.
Figure 14B:
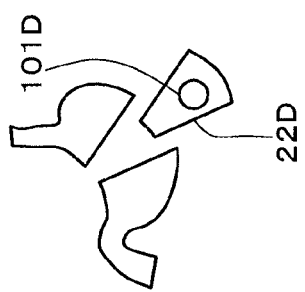
FIG. 14B is a diagram illustrating image processing that is performed by using the surgical assistance apparatus.

In the present embodiment, as clearly shown in FIG. 14B, the region setting unit 12 sets a region that includes an image of the affected part 101D out of the measurement image 21, as the processing candidate region 22D. In this case, the processing candidate region 22D is a region that includes an image of the gastric body of the stomach 115 and from which images of the cardiac part and the pyloric part are excluded. The image data of the measurement image 21D in which the processing candidate region 22D has been set by the region setting unit 12 is output to the processing unit 13.

Figure 14C:
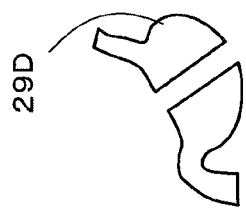
FIG. 14C is a diagram illustrating image processing that is performed by using the surgical assistance apparatus.
Figure 14D:
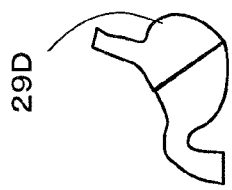
FIG. 14D is a diagram illustrating image processing that is performed by using the surgical assistance apparatus.
Figure 14E:
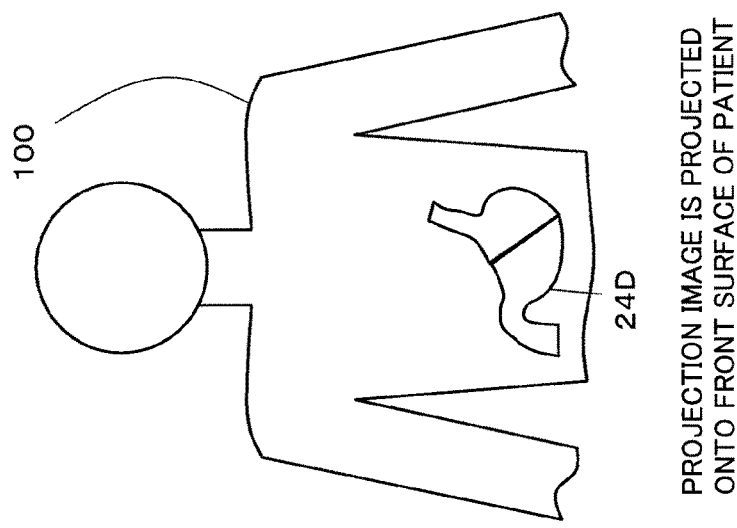
FIG. 14E is a diagram illustrating image processing that is performed by using the surgical assistance apparatus.

As clearly shown in FIG. 14C, the processing unit 13 performs processing to delete the processing candidate region 22D, and subsequently, as shown in FIG. 14D, performs processing to combine images 29D of the stomach 115 other than the processing candidate region 22 out of the measurement image 21D. Thus, the projection image 24D is created. As clearly shown in FIG. 14E, the projection image 24D is projected onto the surface of a portion around the stomach of the patient 100.

In this case, an example of processing related to the surgical assistance apparatus 1 is performed as shown in FIGS. 5, 13, and 14A to 14E. Specifically, in the surgical assistance apparatus 1, when the projection image 24D is to be created, first, measurement data (the measurement image 21D) is obtained by capturing an image of the affected part 101D of the patient 100, using the image capturing apparatus, and then this measurement data is stored in the measurement data storage unit 4 (step S11).

Next, the image processing unit 5 performs image processing based on the measurement data (the measurement image 21D) (step S12). Specifically, the region setting unit 12 sets the processing candidate region 22D. Subsequently, the processing unit 13 creates an image from which the processing candidate region 22D has been deleted, as the projection image 24D (the projection image data).

Next, the image display apparatus 6 retrieves the projection image data from the image processing unit 5 (step S13).

Then, the image display apparatus 6 projects the projection image 24D specified by the projection image data onto the patient 100 on the surgical table 2 (step S14).

With this configuration, when performing a gastrectomy, the surgeon can more accurately check the state that the affected part 101D is to be in after a surgical operation has started, in advance of the surgical operation.

Figure 15:
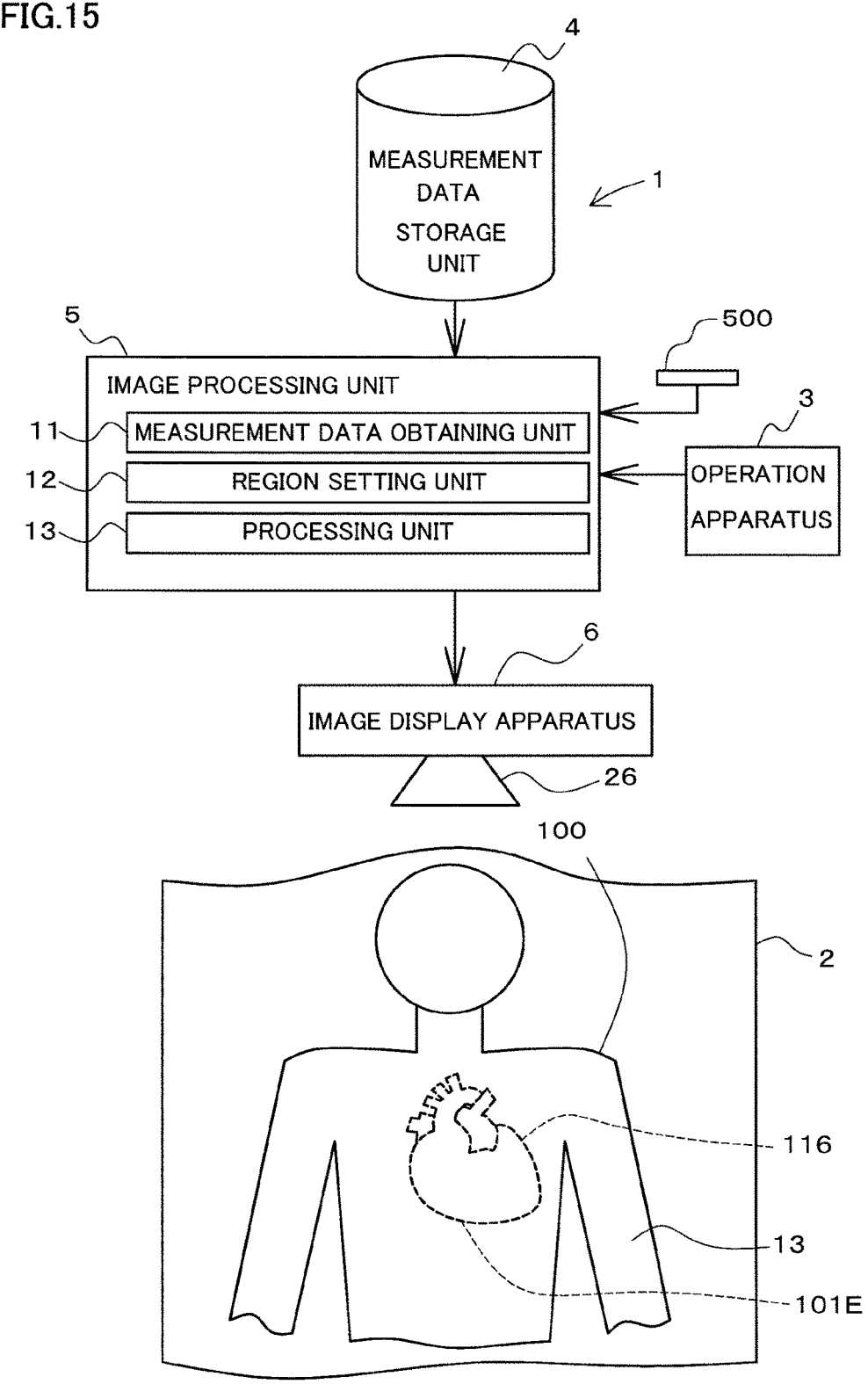
FIG. 15 is a schematic diagram showing the surgical assistance apparatus and the patient.

Also, as shown in FIG. 15, the surgical assistance apparatus 1 may be used when the Batista procedure (a partial left ventriculectomy), which is a partial removal of a heart 116 of the patient 100 on the surgical table 2, is performed. FIG. 15 is a schematic diagram showing the surgical assistance apparatus 1 and the patient 100.

FIGS. 16A to 16E are diagrams illustrating image processing that is performed by using the surgical assistance apparatus 1. As shown in FIGS. 15 and 16A to 16E, in the present embodiment, the measurement data storage unit 4 stores measurement data that has been obtained by measuring an affected part 101E of the patient 100, before a surgical operation is started. In the present embodiment, the measurement data is image data that has been obtained by capturing an image of a portion around the heart 116 of the patient 100, including the affected part 101E, from the front side of the patient 100, by using the above-described image capturing apparatus.

The image processing unit 5 creates a postoperative image of the affected part as a projection image 24E. Specifically, in the present embodiment, the image processing unit 5 is configured to receive measurement data that specifies measurement image 21E that includes an image of the heart 116 of the patient 100.

The region setting unit 12 is configured to set a predetermined processing candidate region 22E out of the measurement image 21E.

Figure 16A:
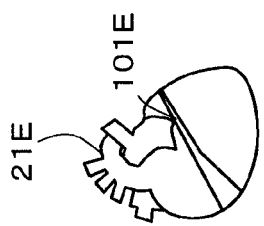
FIG. 16A is a diagram illustrating image processing that is performed by using the surgical assistance apparatus.
Figure 16B:
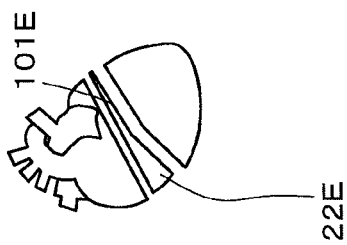
FIG. 16B is a diagram illustrating image processing that is performed by using the surgical assistance apparatus.

In the present embodiment, as clearly shown in FIG. 16B, the region setting unit 12 sets a region that includes an image of the affected part 101E out of the measurement image 21E, as the processing candidate region 22E. In this case, the processing candidate region 22E includes a portion around the left ventricle. The image data of the measurement image 21E in which the processing candidate region 22E has been set by the region setting unit 12 is output to the processing unit 13.

Figure 16C:
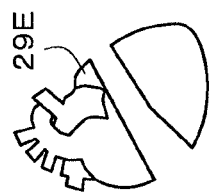
FIG. 16C is a diagram illustrating image processing that is performed by using the surgical assistance apparatus.
Figure 16D:
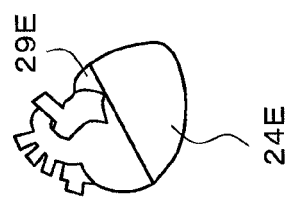
FIG. 16D is a diagram illustrating image processing that is performed by using the surgical assistance apparatus.
Figure 16E:
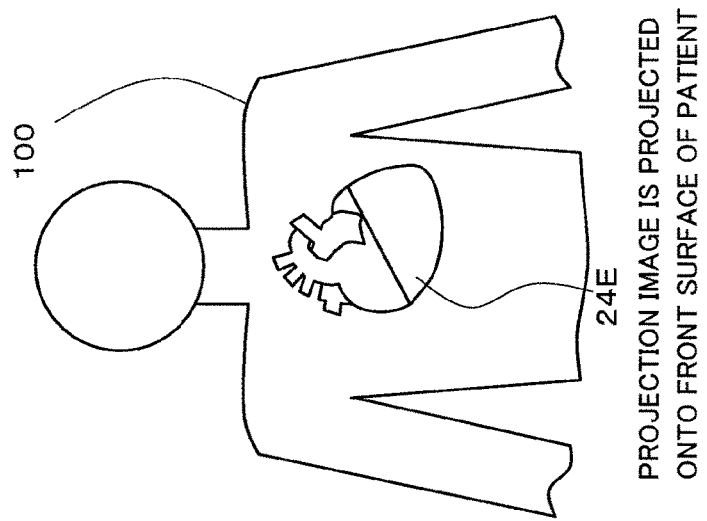
FIG. 16E is a diagram illustrating image processing that is performed by using the surgical assistance apparatus.

As clearly shown in FIG. 16C, the processing unit 13 performs processing to delete the processing candidate region 22E, and subsequently, as shown in FIG. 16D, performs processing to combine images 29E of the heart 116 other than the processing candidate region 22E out of the measurement image 21E. Thus, the projection image 24E is created. As clearly shown in FIG. 16E, the projection image 24E is projected onto the surface of a portion around the heart 116 of the patient 100.

In this case, an example of processing related to the surgical assistance apparatus 1 is performed as shown in FIGS. 5, 15, and 16A to 16E. Specifically, in the surgical assistance apparatus 1, when the projection image 24E is to be created, first, measurement data (the measurement image 21E) is obtained by capturing an image of the affected part 101E of the patient 100, using the image capture apparatus, and then this measurement data is stored in the measurement data storage unit 4 (step S11).

Next, the image processing unit 5 performs image processing based on the measurement data (the measurement image 21E) (step S12). Specifically, the region setting unit 12 sets the processing candidate region 22E. Subsequently, the processing unit 13 creates an image from which the processing candidate region 22E has been deleted, as the projection image 24E (the projection image data).

Next, the image display apparatus 6 retrieves the projection image data from the image processing unit 5 (step S13). Then, the image display apparatus 6 projects the projection image 24E specified by the projection image data onto the patient 100 on the surgical table 2 (step S14).

With this configuration, when performing the Batista procedure, the surgeon can more accurately check the state that the affected part 101E is to be in after a surgical operation has started, in advance of the surgical operation.

Although embodiments of the present invention have been described above, the present invention is not limited to the above-described embodiments, and may be variously modified within the scope of the claims. According to the present invention, the image processing unit is configured to create projection image data based on measurement data that has been obtained by measuring an affected part of a patient, and thus create a projection image as an image that is specified by the projection image data. The projection image is an image that is to be projected onto the patient, and is required to include an image that shows the affected part after a surgical operation has started. The projection image may be created by using an actual image of the patient, or by using a schematic image.

INDUSTRIAL APPLICABILITY

The present invention is broadly applicable, as a surgical assistance apparatus, a program, a storage medium, and a surgical assistance method.

DESCRIPTIONS OF REFERENCE NUMERALS

1: Surgical assistance apparatus
3: Operation apparatus
5: Image processing unit
6: Image display apparatus
12: Region setting unit
13: Processing unit
15: Indicator
22, 22C, 22D, 22E: Processing candidate region
23, 23C: Processed image
24, 24A, 24B, 24C, 24D, 24E: Projection image
28: Osteotomy line
100: Patient
101C, 101D, 101E: Affected part
105: Femur
106: Tibia
108: Anterior superior iliac spine (Referential body part of patient)
110: Center point of caput
113: Center point of ankle
114: Center point of knee joint
200: Knee joint implant (Implant)
221, 221C: First processing candidate region
222, 222C: Second processing candidate region
500: Storage medium

What is claimed is:

1. A surgical assistance apparatus for a knee joint operation comprising:
  a projector;
  a data storage device; and
  a Central Processing Unit (CPU) that is communicatively coupled to the projector and the data storage device, wherein the CPU:

stores, in the data storage device, measurements of a knee joint of a patient;

creates a predetermined image projection data based on the measurements of the knee joint of the patient stored in the data storage device, determines an intraoperative image of the knee joint of the patient and a postoperative image of the knee joint of the patient based on the predetermined image projection data, creates a projection image based on the predetermined image data, wherein the projection image may include at least one of the intraoperative image of the knee joint of the patient and the postoperative image of the knee join of the patient, determines, in advance of a surgical operation, alignment parameters to align the projection image on to the patient, projects, using the projector, the projection image onto the patient based on the alignment parameters, sets predetermined processing candidate regions from parts of a measurement image that is specified by the measurements of the knee joint of the patient, creates a predetermined processed image by applying predetermined processing to the processing candidate regions, and subsequently creates the projection image by combining the predetermined processed image with an image other than the processing candidate regions, receives the measurements of the knee joint of the patient that includes an image of a femur and an image of a tibia of the patient, sets a first processing candidate region that includes the image of the femur, and a second processing candidate region that includes the image of the tibia, and creates the processed image by rotating the processing candidate region.

2. The surgical assistance apparatus according to claim 1, wherein the CPU receives the measurements of the knee joint of the patient that specifies the measurement image that includes the image of the femur and the image of the tibia of the patient, and creates the projection image in which a center point of a caput, a center point of the knee joint, and a center point of an ankle in the measurement image are shown so as to be aligned in a straight line.

3. The surgical assistance apparatus according to claim 1, wherein the CPU creates the projection image such that the projection image includes an image of an indicator that is provided on a body part that serves as a referential body part of the patient when the measurement image is captured.

4. The surgical assistance apparatus according to claim 1, wherein the CPU creates, as the projection image, an image for which the measurements of the knee joint of the patient is yet to be processed.

5. The surgical assistance apparatus according to claim 1, wherein the CPU creates, as the projection image, an image that includes at least one of:
an image of an implant that is placed in the knee joint; and
an osteotomy line.

6. The surgical assistance apparatus according to claim 1:
wherein the CPU receives operation data that operates the measurements of the knee joint of the patient; and
displays, via the projector, the projection image onto the patient.

7. A surgical assistance method for a knee joint operation comprising:

storing, in a data storage device, measurements of a knee joint of a patient;

creating predetermined image projection data, via a Central Processing Unit (CPU) that is communicatively coupled to a projector and the data storage device, based on measurements of the knee joint of the patient stored in the data storage device, determining an intraoperative image of the knee joint and a postoperative image of the knee joint based on the predetermined image projection data, creating, a projection image based on the predetermined image data, wherein the projection image may include at least one of the intraoperative image of the knee joint of the patient and the postoperative image of the knee joint of the patient, determining, in advance of a surgical operation, alignment parameters to align the projection image on to the patient, and projecting, using the projector, the projection image onto the patient based on the alignment parameters, setting predetermined processing candidate regions from parts of a measurement image that is specified by the measurements of the knee joint of the patient, creating a predetermined processed image by applying predetermined processing to the processing candidate regions, and subsequently creating the projection image by combining the predetermined processed image with an image other than the processing candidate regions out of the measurement image, receiving the measurements of the knee joint of a patient that specifies the measurement image that includes an image of a femur and an image of a tibia of the patient, setting a first processing candidate region that includes the image of the femur and a second processing candidate region that includes the image of the tibia, and creating the processed image by rotating the processing candidate region.

* * * * *